(12) United States Patent
Narducci et al.

(10) Patent No.: US 11,903,592 B2
(45) Date of Patent: Feb. 20, 2024

(54) DATA MODULES FOR SURGICAL INSTRUMENTS

(71) Applicant: DePuy Synthes Products, Inc., Raynham, MA (US)

(72) Inventors: David S. Narducci, Jupiter, FL (US); Jon Edwards, Stuart, FL (US); Matthew S. Wallace, Wellington, FL (US); Claudia Orozco-Kirkman, Palm Beach Gardens, FL (US); Cedric Beausse, Greenacres, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 284 days.

(21) Appl. No.: 17/316,203

(22) Filed: May 10, 2021

(65) Prior Publication Data
US 2022/0354509 A1  Nov. 10, 2022

(51) Int. Cl.
| | |
|---|---|
| A61B 17/16 | (2006.01) |
| A61B 17/14 | (2006.01) |
| A61B 17/92 | (2006.01) |
| A61B 17/00 | (2006.01) |
| A61B 17/56 | (2006.01) |

(52) U.S. Cl.
CPC ........ *A61B 17/1626* (2013.01); *A61B 17/142* (2016.11); *A61B 17/92* (2013.01); *A61B 2017/0023* (2013.01); *A61B 2017/00115* (2013.01); *A61B 2017/00199* (2013.01); *A61B 2017/00398* (2013.01); *A61B 2017/00477* (2013.01); *A61B 2017/564* (2013.01); *A61B 2017/922* (2013.01)

(58) Field of Classification Search
CPC ..... A61B 17/14; A61B 17/142; A61B 17/144; A61B 17/16; A61B 17/1622; A61B 17/1624; A61B 17/1626; A61B 17/1628; A61B 17/92; A61B 2017/00017; A61B 2017/00115; A61B 2017/00128; A61B 2017/00199; A61B 2017/0023; A61B 2017/922
See application file for complete search history.

(56) References Cited

U.S. PATENT DOCUMENTS

| | | |
|---|---|---|
| 6,854,642 B2 | 2/2005 | Metcalf et al. |
| 7,123,128 B2 | 10/2006 | Mullet et al. |
| 7,298,240 B2 | 11/2007 | Lamar |
| 8,114,345 B2 | 2/2012 | Dlugos, Jr. et al. |

(Continued)

FOREIGN PATENT DOCUMENTS

| | | |
|---|---|---|
| CN | 114367947 A | 4/2022 |
| WO | WO-2021015606 A1 | 1/2021 |

OTHER PUBLICATIONS

International Search Report and Written Opinion for Intl. Pat. App. No. PCT/IB2022/054173 dated Aug. 16, 2022.

*Primary Examiner* — Eric S Gibson

(57) ABSTRACT

In general, data modules for surgical instruments and methods of using data modules for surgical instruments are provided. In an exemplary embodiment, a data module is configured to be removably attached to a powered surgical tool such as an electrosurgical tool. The data module is a standalone device including electronic components that are configured to, with the data module attached to the electrosurgical tool, interact with the electrosurgical tool.

28 Claims, 10 Drawing Sheets

(56) References Cited

U.S. PATENT DOCUMENTS

| | | | |
|---|---|---|---|
| 8,393,409 B2 | 3/2013 | Pedicini | |
| 8,695,726 B2 | 4/2014 | Pedicini | |
| 8,925,812 B2 | 1/2015 | Schmucker et al. | |
| 8,936,105 B2 | 1/2015 | Pedicini | |
| 9,095,346 B2 | 8/2015 | Houser et al. | |
| 9,155,659 B2 | 10/2015 | Walter et al. | |
| 9,468,447 B2 | 10/2016 | Aman et al. | |
| 10,175,096 B2 | 1/2019 | Dickerson | |
| 10,255,995 B2 | 4/2019 | Ingmanson | |
| 10,437,228 B2 | 10/2019 | Kreuzer et al. | |
| 11,278,297 B2 * | 3/2022 | Hines | A61B 90/06 |
| 11,553,931 B2 * | 1/2023 | Marek | A61B 17/1622 |
| 2008/0281301 A1 | 11/2008 | DeBoer et al. | |
| 2013/0161050 A1 | 6/2013 | Pedicini | |
| 2013/0253499 A1 * | 9/2013 | Kimball | A61B 90/98 |
| | | | 606/1 |
| 2016/0184016 A1 | 6/2016 | Albright | |
| 2016/0192989 A1 | 7/2016 | Aman | |
| 2018/0055552 A1 | 3/2018 | Pedicini | |
| 2018/0055554 A1 | 3/2018 | Pedicini | |
| 2019/0013830 A1 * | 1/2019 | Hoglund | A61B 90/90 |
| 2019/0183555 A1 | 6/2019 | Pedicini | |
| 2020/0222061 A1 * | 7/2020 | Hines | A61B 17/162 |
| 2021/0068795 A1 * | 3/2021 | Nikou | A61B 34/20 |
| 2021/0113218 A1 * | 4/2021 | Marek | A61B 17/1622 |
| 2021/0145477 A1 * | 5/2021 | Shaw | A61B 17/3403 |
| 2021/0212769 A1 * | 7/2021 | Walen | A61B 34/76 |
| 2021/0322055 A1 * | 10/2021 | Lindekugel | A61B 17/1626 |
| 2022/0168038 A1 * | 6/2022 | Shelton, IV | A61B 17/07207 |
| 2022/0354509 A1 * | 11/2022 | Narducci | A61B 17/1626 |

* cited by examiner

DATA MODULES FOR SURGICAL INSTRUMENTS

FIELD

The present disclosure generally relates to data modules for surgical instruments.

BACKGROUND

Powered surgical tools, such as those using battery power, have provided increased convenience and productivity to medical professionals in surgical settings. Powered surgical tools are typically sterilized before utilization to help ensure patient safety. Powered surgical tools are thus typically designed to withstand the temperatures, moisture levels, and pressures associated with sterilization techniques for sterilizing surgical tools, such as autoclaving. However, some electronic components are incapable of being subjected to the temperatures, moisture levels, and pressures of sterilization without losing their functionality. Powered surgical tools thus cannot include such electronic components even through the electronic components would provide various benefits to use of the powered surgical tool.

Accordingly, there remains a need for improved powered surgical tools.

SUMMARY

In general, data modules for surgical instruments and methods of using data modules for surgical instruments are provided.

In one aspect, a surgical system is provided that in one embodiment includes an electrosurgical tool and a data module. The electrosurgical tool includes a controller. The data module is configured to be removably attached to the electrosurgical tool and includes a light, a memory, and a communication mechanism. With the data module removably attached to the electrosurgical tool, the controller of the electrosurgical tool is configured to control illumination of the light to indicate a condition of the electrosurgical tool, and the data module is configured to receive information from the electrosurgical tool regarding the electrosurgical tool and to store the received information in the memory. The communication mechanism of the data module is configured to communicate data stored in the memory to an external device.

The surgical system can have any number of variations. For example, the memory can be configured to store therein data regarding a patient with which the electrosurgical tool is to be used, and the controller of the electrosurgical tool can be configured to adjust a setting of the electrosurgical tool based on the data regarding the patient. For another example, the information received from the electrosurgical tool can include identification information that identifies the electrosurgical tool, and the information received from the electrosurgical tool can include tool information retrieved from the electrosurgical tool based on the received identification information.

For yet another example, the information received from the electrosurgical tool can include data regarding operation of the electrosurgical tool in real time with use of the electrosurgical tool on a patient. In some embodiments, the external device can be configured to determine, using the data received from the data module, whether the electrosurgical tool is in a state satisfactory for use on another patient subsequent to the use on the patient; and/or the memory can be configured to store therein data regarding a patient with which the electrosurgical tool is to be used, and the external device can be configured to analyze, using the data regarding the patient and the data received from the data module, the use of the electrosurgical tool on the patient.

For still another example, the information received from the electrosurgical tool can include serial data that uniquely identifies the electrosurgical tool.

For another example, the condition can be one of a plurality of possible conditions of the electrosurgical tool, and the illumination of the light can be different based on the condition being indicated. In some embodiments, the illumination of the light can be different in at least one of color and whether the light is blinking or continuously illuminated, and the plurality of conditions include at least two of temperature, status of a power source of the electrosurgical tool, an energy mode of the electrosurgical tool, and operational status of the electrosurgical tool.

For still another example, the condition can be selected from the group consisting of temperature, status of a power source of the electrosurgical tool, an energy mode of the electrosurgical tool, and operational status of the electrosurgical tool. For another example, the electrosurgical tool can include a slot configured to releasably seat the data module therein. For yet another example, the electrosurgical tool can include a mating feature, and the data module can include a mating element configured to releasably mate with the mating feature to removably attach the data module and the electrosurgical tool.

For another example, the external device can be configured to have an app stored thereon that is configured to manage the data received via the communication mechanism of the data module. In some embodiments, the external device can be configured to communicate data regarding a patient to the communication mechanism of the data module, the data module can be configured to store the received data regarding the patient in the memory, and the controller of the electrosurgical tool can be configured to adjust at least one setting of the electrosurgical tool based on the stored data regarding the patient.

For yet another example, the data module can include a printed circuit board (PCB). For still another example, the data module can include a display configured to show information thereon indicative of the information received from the electrosurgical tool regarding the electrosurgical tool. For another example, the electrosurgical tool can be configured to be sterilized and reused, and the light can be configured to not be operational if sterilized.

For still another example, the data module can include a housing that houses the light, the memory, and the communication mechanism. In some embodiments, the electrosurgical tool can include a slot configured to releasably seat the housing therein; and/or the electrosurgical tool can include a mating feature, and the data module can include a mating element configured to releasably mate with the mating feature to removably attach the data module and the electrosurgical tool.

For yet another example, the communication mechanism can be configured to communicate using Near Field Communication (NFC). For another example, the light can include a light emitting diode (LED). For still another example, the electrosurgical tool can be one of an orthopedic impactor, a surgical drill, and a surgical reciprocating saw.

In another embodiment, a surgical system is provided that includes a disposable housing configured to be removably attached to an electrosurgical tool, a light configured to illuminate to indicate a condition of the electrosurgical tool to which the housing is removably attached, a memory configured to store data therein received from the electrosurgical tool regarding use of the electrosurgical tool to which the housing is removably attached, and a communication mechanism configured to communicate the data stored in the memory to an external device.

The surgical system can vary in any number of ways. For example, with the housing removably attached to the electrosurgical tool, the illumination of the light can be configured to be controlled by the electrosurgical tool.

For another example, the condition can be one of a plurality of possible conditions of the electrosurgical tool, and the illumination of the light can be different based on the condition being indicated. In some embodiments, the illumination of the light can be different in at least one of color and whether the light is blinking or continuously illuminated, and the plurality of conditions can include at least two of temperature, status of a power source of the electrosurgical tool, an energy mode of the electrosurgical tool, and operational status of the electrosurgical tool.

For yet another example, the condition can be selected from the group consisting of temperature, status of a power source of the electrosurgical tool, an energy mode of the electrosurgical tool, and operational status of the electrosurgical tool. For another example, the memory can be configured to store therein data received from the electrosurgical tool that includes serial data that uniquely identifies the electrosurgical tool. For still another example, with the housing removably attached to the electrosurgical tool, information received from the electrosurgical tool regarding the electrosurgical tool can be configured to be stored in the memory, and the communication mechanism can be configured to communicate the information stored in the memory to the external device. For yet another example, the external device can be configured to transmit data to the communication mechanism for storage in the memory, and the transmitted data can regard a patient with which the electrosurgical tool is to be used.

For another example, the external device can be configured to have an app stored thereon that is configured to manage the data received via the communication mechanism. In some embodiments, the external device can be configured to communicate data regarding a patient to the communication mechanism, and the memory can be configured to store therein the received data regarding the patient.

For yet another example, a display can be attached to the housing and can be configured to show information thereon indicative of information received from the electrosurgical tool regarding the electrosurgical tool. For another example, the communication mechanism can be configured to communicate using NFC. For still another example, the light can include an LED.

For still another example, the surgical system can also include the electrosurgical tool. In some embodiments, the electrosurgical tool can include a slot configured to releasably seat the housing therein; the electrosurgical tool can include a mating feature, and the housing includes a mating element configured to releasably mate with the mating feature to removably attach the housing and the electrosurgical tool; with the housing removably attached to the electrosurgical tool, a controller of the electrosurgical tool can be configured to control illumination of the light to indicate the condition of the electrosurgical tool the electrosurgical tool; the memory can be configured to store therein data regarding a patient with which the electrosurgical tool is to be used, and, with the housing removably attached to the electrosurgical tool, a controller of the electrosurgical tool can be configured to adjust at least one setting of the electrosurgical tool based on the data regarding the patient; the electrosurgical tool can be one of an orthopedic impactor, a surgical drill, and a surgical reciprocating saw; the electrosurgical tool can be configured to be sterilized and reused; and/or the housing can be disposable after a single use, and the light can be configured to not be operational if sterilized.

In another aspect, a surgical method is provided that in one embodiment includes, during use of an electrosurgical tool in a surgical procedure, an electronic controller of the electrosurgical tool controlling illumination of a light of a data module that is removably and mechanically attached to the electrosurgical tool, and causing data regarding operation of the electrosurgical tool in the surgical procedure to be communicated to a memory of the data module for storage in the memory. The illumination of the light indicates a condition of the electrosurgical tool.

The surgical method can vary in any number of ways. For example, the surgical method can also include the controller adjusting a setting of the electrosurgical tool based on data stored in the memory regarding a patient with which the electrosurgical tool is being used in the surgical procedure.

For another example, the condition can be one of a plurality of possible conditions of the electrosurgical tool, and the illumination of the light can be different based on the condition being indicated. In some embodiments, the illumination of the light can be different in at least one of color and whether the light is blinking or continuously illuminated, and the plurality of conditions can include at least two of temperature, status of a power source of the electrosurgical tool, an energy mode of the electrosurgical tool, and operational status of the electrosurgical tool.

For yet another example, the condition can be selected from the group consisting of temperature, status of a power source of the electrosurgical tool, an energy mode of the electrosurgical tool, and operational status of the electrosurgical tool. For still another example, the surgical method can also include, during the use of the electrosurgical tool in the surgical procedure, the controller causing a display of the data module to show information thereon regarding the use of the electrosurgical tool.

For another example, the surgical method can also include, after removal of the data module from the electrosurgical tool, transmitting the stored data to an external device. In some embodiments, the external device can be configured to determine, using the data transmitted to the external device, whether the electrosurgical tool is in a state satisfactory for use in a second, subsequent surgical procedure.

For yet another example, the data module can be disposable, the light can be configured to not be operational if sterilized, and the surgical method can also include, after removal of the data module from the electrosurgical tool, sterilizing the electrosurgical tool. For still another example, the data module can be removably and mechanically attached to the electrosurgical tool by being seated in a slot formed in the electrosurgical tool. For another example, the electrosurgical tool can include a mating feature, and the data module can include a mating element releasably mated with the mating feature to removably and mechanically attach the data module and the electrosurgical tool. For still another example, the electrosurgical tool can be one of an orthopedic impactor, a surgical drill, and a surgical reciprocating saw.

BRIEF DESCRIPTION OF DRAWINGS

This disclosure will be more fully understood from the following detailed description taken in conjunction with the accompanying drawings, in which.

DETAILED DESCRIPTION

Figures 1, 2:
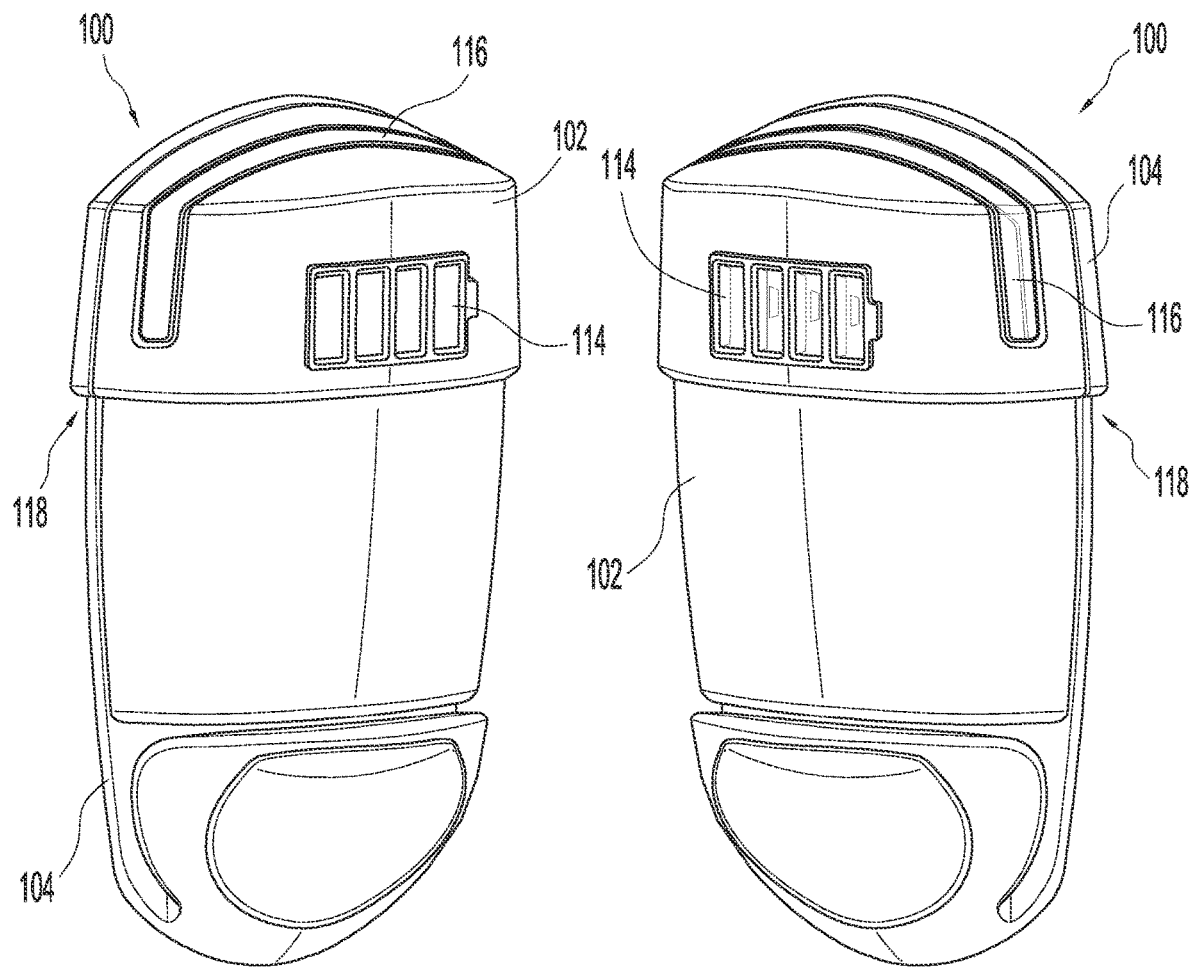
FIG. 1 is a perspective view of one embodiment of a data module.
FIG. 2 is another perspective view of the data module of FIG. 1.
Figure 3:
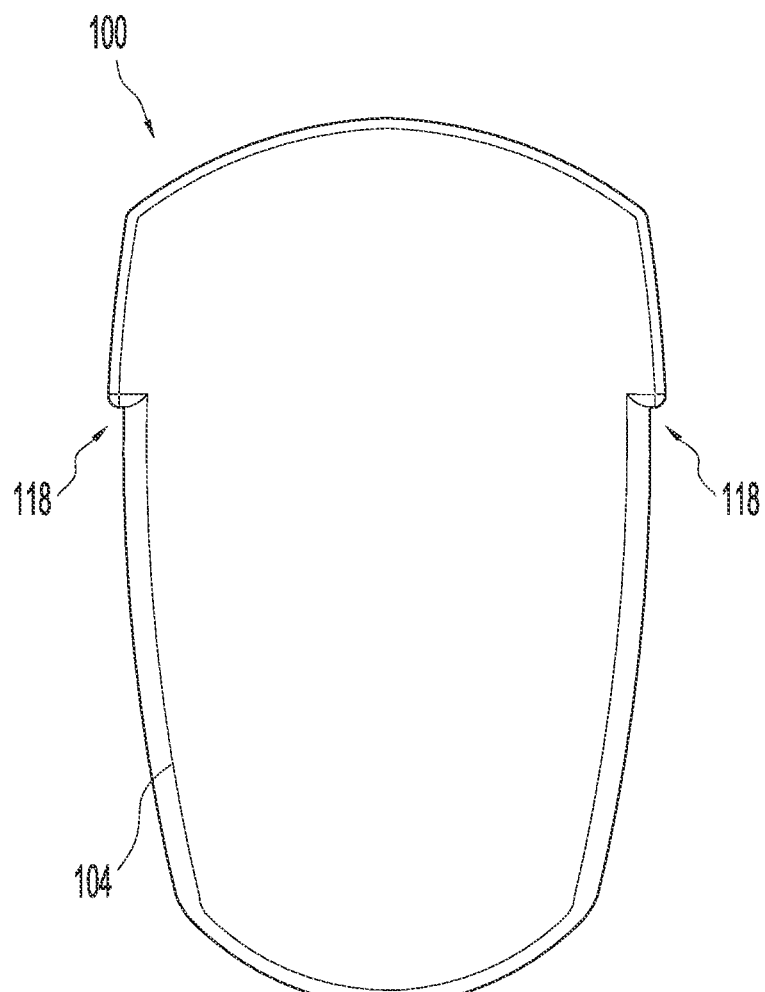
FIG. 3 is a back view of the data module of FIG. 1.
Figure 4:
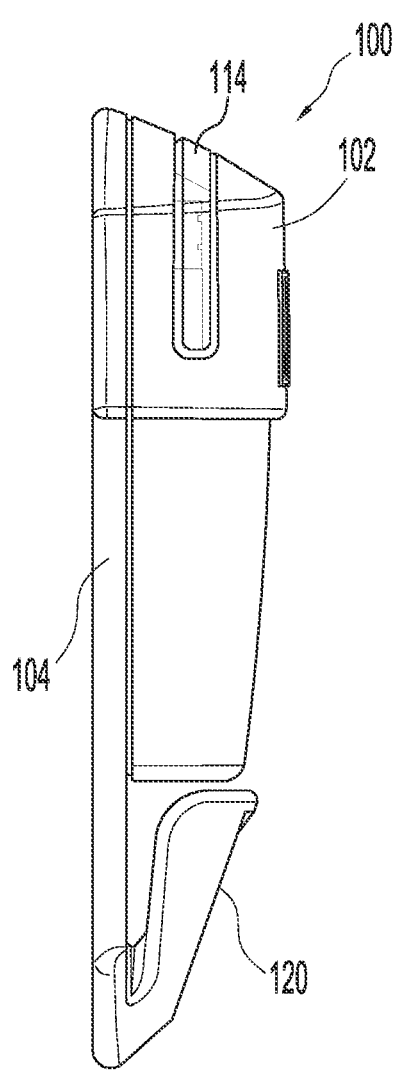
FIG. 4 is a side view of the data module of FIG. 1.
Figure 5:
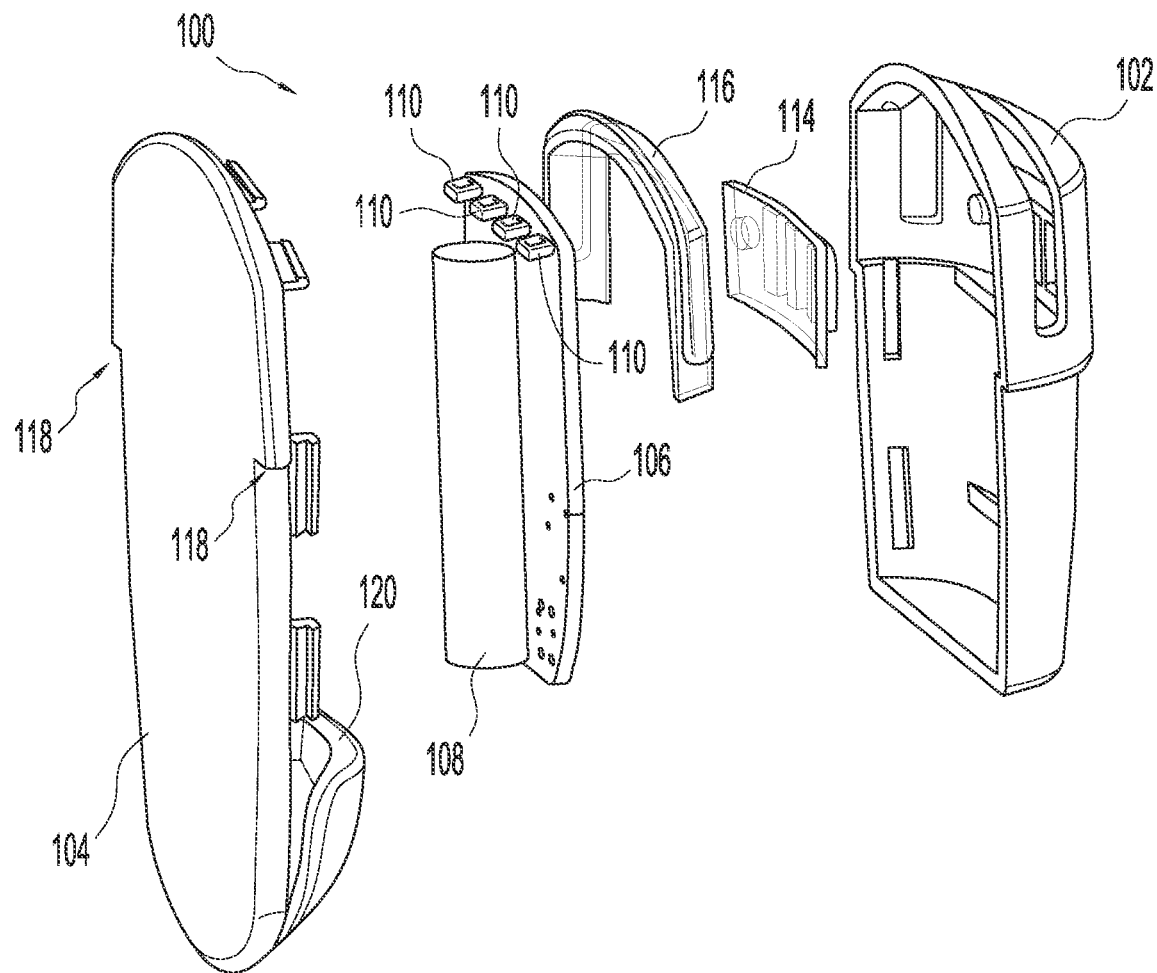
FIG. 5 is an exploded view of the data module of FIG. 1.
Figure 6:
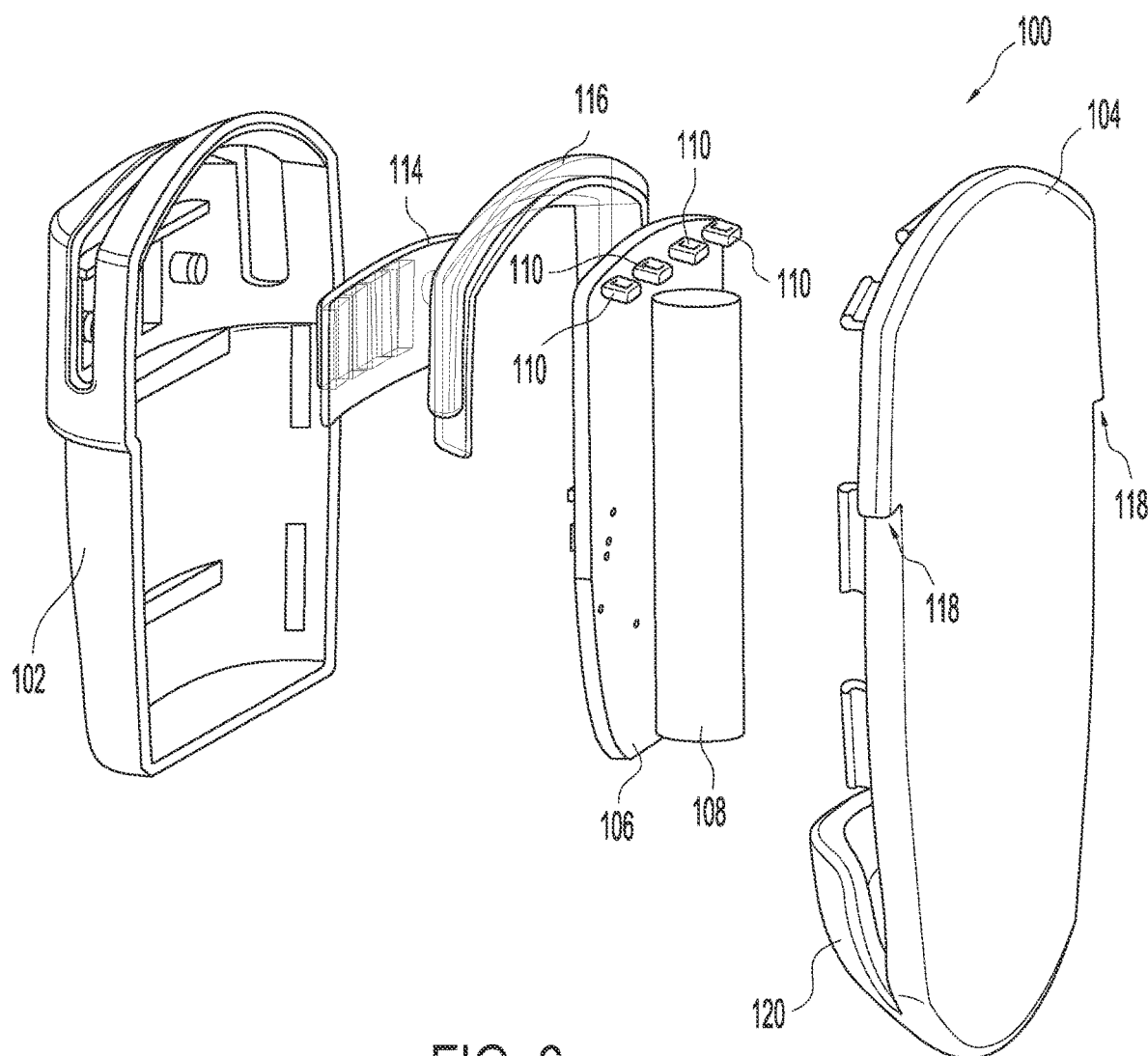
FIG. 6 is another exploded view of the data module of FIG. 1.
Figure 7:
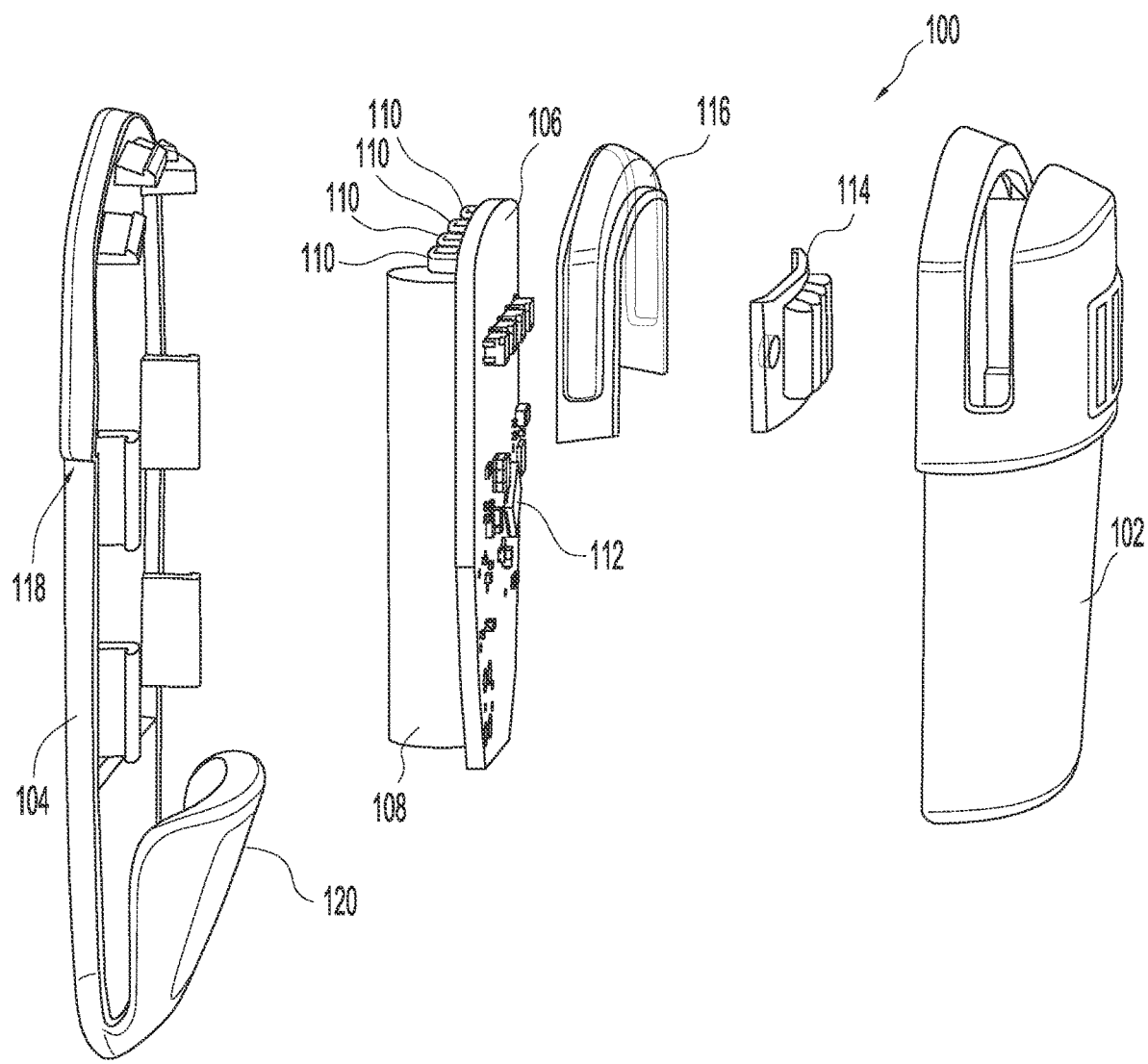
FIG. 7 is yet another exploded view of the data module of FIG. 1.
Figure 8:
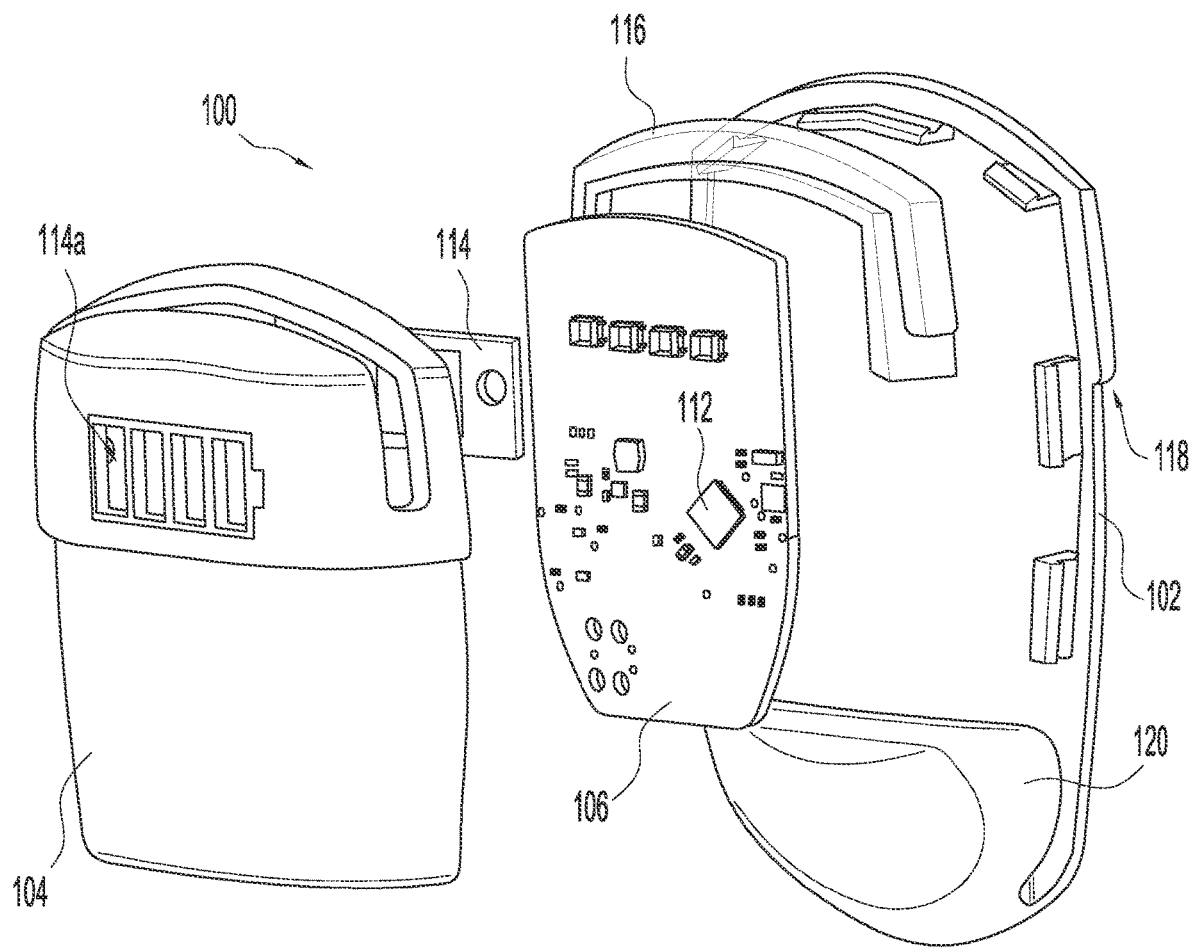
FIG. 8 is still another exploded view of the data module of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, data modules for surgical instruments and methods of using data modules for surgical instruments are provided. In an exemplary embodiment, a data module is configured to be removably attached to a powered surgical tool such as an electrosurgical tool. The data module is a standalone device including electronic components that are configured to, with the data module attached to the electrosurgical tool, interact with the electrosurgical tool. The data module can thus provide functionality that would otherwise not be available for the electrosurgical tool and/or that would be more difficult without the data module.

One example of functionality that can be provided using the data module is use of a light. The data module's electronic components can include a light configured to provide information regarding a condition of the electrosurgical tool, with different illuminations (e.g., different colors and/or blinking versus continuous illumination) of the light indicating different conditions such as temperature, status of a power source of the electrosurgical tool, an energy mode of the electrosurgical tool, and operational status of the electrosurgical tool. Electrosurgical tools are typically reusable devices that are sterilized before each use to help ensure patient safety. Lights, such as LEDs and other low power lights, are unable to withstand the sterilization environment that is effective for sterilizing surgical tools, so reusable, sterilizable electrosurgical tools cannot include any lights because the light's functionality would be impaired or destroyed in the sterilization process. Even if a light manages to maintain functionality after a sterilization process, reusable, sterilizable electrosurgical tools are repeatedly subjected to sterilization, e.g., after each use of the tool. The light being subjected to the repeated sterilizations will eventually impair or destroy the light's functionality before an end of the tool's useful, otherwise functional life even if the light's functionality if not impaired or destroyed in the first sterilization or a number of sterilizations successive to the first sterilization. A light may be hermetically sealed and included in an electrosurgical tool subjected to sterilization, but hermetic sealing is expensive and is thus not a desirable solution to providing an electrosurgical tool with a light. The data module including a light allows a light to be provided on the electrosurgical tool and for the light to be provided without hermetic sealing. The light being on the electrosurgical tool, via the data module, may help a user of the electrosurgical tool easily see information about the electrosurgical tool that otherwise would have been unavailable or would not have been available without the user having to less conveniently receive such information elsewhere, such as via an audible signal that may be obscured by other noise, on a display screen in an operating room, etc. The light is configured to be controlled by the electrosurgical tool, e.g., by an electronic controller of the electrosurgical tool. The data module therefore does not have to include programming and related hardware for controlling the light, which may help reduce a size of the data module, help simplify manufacturing of the data module, and/or help reduce overall cost of the data module. The data module is configured to be disposable, e.g., disposed of (as waste and/or for recycling) after a single use with a single electrosurgical tool in a single surgical procedure, so as to not be subjected to sterilization that would ruin the light's functionality.

Another example of functionality that can be provided using the data module is electrosurgical tool control. Data regarding a patient can be stored on the data module, e.g., in a memory thereof. With the data module removably attached to an electrosurgical tool, the data regarding the patient can be communicated to the electrosurgical tool, which can then use the data to control one or more electronic control parameters of the electrosurgical tool, such as a speed or an impact force of the electrosurgical tool. The electrosurgical tool's use may thus be adjusted to the particular patient, which may help prevent patient harm. The data regarding a patient can include diagnosis information regarding the patient that can affect the electrosurgical tool's use on the patient. For example, the diagnosis information can include if the patient has arthritis or osteoporosis, which may make a particular device's use on bone more dangerous if the speed of bone drilling, speed of bone cutting, force of bone impacting, etc. is not constrained to be below or above (as appropriate for the parameter being controlled) a predetermined threshold. The data regarding a patient can include bone quality information, which may make a particular device's use on bone more dangerous if the speed of bone drilling, speed of bone cutting, force of bone impacting, etc. is not constrained to be below or above (as appropriate for the parameter being controlled) a predetermined threshold. The data regarding a patient can include a height of the patient, which may help the electrosurgical tool set a maximum length of time for bone drilling and/or bone cutting based on a typical bone size for that height.

Another example of functionality that can be provided using the data module is performance analysis. The data module can be configured to receive data gathered by the electrosurgical tool regarding use of the electrosurgical tool in real time with the use of the electrosurgical tool. Examples of such data include temperature data, duration of the electrosurgical tool's use, motor speed data, power source usage and/or level, energy mode, drilling speed, cutting speed, impact force, and other types of data. The data module can include a memory configured to store the data received from the electrosurgical tool. The data module can also include a communication mechanism configured to communicate data stored at the data module to an external device that is external to the data module, such as a mobile phone, an electronic tablet, a laptop computer, a desktop computer, or other computer system. The external device can use the data received from the data module to analyze use of the electrosurgical tool, which may facilitate the patient's post-surgical treatment, help a surgeon or other user evaluate the electrosurgical tool's performance and/or their own performance, and/or help a manufacturer evaluate use of a electrosurgical tool in different surgical procedures and/or by different users by receiving multiple data sets from multiple data modules each used with the same electrosurgical tool and/or each used with the same type of electrosurgical tool.

Another example of functionality that can be provided using the data module is proactive tool maintenance. Analysis of data stored at the data module, e.g., the data discussed above that can be stored at the data module during use of an electrosurgical tool to which the data module is removable attached, may help a manufacturer or other entity determine that the electrosurgical tool is in need of maintenance before the electrosurgical tool experiences failure. The manufacturer or other entity can thus contact a purchaser, user, owner, and/or other appropriate party to indicate that, e.g., the electrosurgical tool needs maintenance and should be returned to the manufacturer or other entity for repair or replacement. The electrosurgical tool can thus be repaired or replaced before the electrosurgical tool experiences failure, which may help eliminate delays incurred during performance of a surgical procedure by having to replace a malfunctioning electrosurgical tool, help increase customer satisfaction, and/or help prolong a life of the electrosurgical tool. For example, the data may indicate that an electrosurgical tool's on-board power source is depleted, does not have enough remaining power for a next use of the electrosurgical tool, or is being depleted unusually rapidly, in which case the electrosurgical tool's power source can be replaced or another electrosurgical tool can be provided. For another example, the data may indicate that an electrosurgical tool's sensor (e.g., temperature sensor, pressure sensor, proximity sensor, force sensor, etc.) is not gathering data properly, in which case the sensor can be repaired or replaced, or another electrosurgical tool can be provided.

Other examples of functionality that can be provided using the data module are tool tracking and fee services. As mentioned above, electrosurgical tools are typically reusable. A purchaser, e.g., a hospital, a teaching facility, etc., can purchase an electrosurgical tool for an upfront fee from a seller, e.g., a manufacturer of the electrosurgical tool, an authorized distributer for a manufacturer of the electrosurgical tool, etc. In such situations, the seller does not know, cannot easily know, or learns after a significant time delay, how many times the electrosurgical tool is used after purchase. As also mentioned above, the data module is configured to be disposable. Being configured for single use before being disposed, tracking data module sales and/or tracking data received from sold data modules can allow a seller to track a number of times an electrosurgical tool is used by a particular purchaser based on a number of data modules sold to the purchaser and/or based on a number of data sets received from the purchaser's data modules with each data module data set corresponding to a single electrosurgical tool use. Knowing a number of times an electrosurgical tool is used may help a manufacturer evaluate pricing for the electrosurgical tool and/or evaluate durability of the electrosurgical tool. Since data can be retrieved from the data module very soon after the data module's use with an electrosurgical tool, and in at least some instances when the data module is still removably attached to the electrosurgical tool, usage data can be quickly received.

The data modules described herein can be used with any of a variety of powered surgical tools. In an exemplary embodiment, the powered surgical tool is an electrosurgical tool such as an orthopedic impactor, a surgical drill, or a surgical reciprocating saw.

FIGS. 1-8 illustrate one embodiment of a data module 100 configured to removably attach to a powered surgical tool such as an electrosurgical tool. The data module 100 is configured to be disposable.

The data module 100 includes a housing configured to house all components of the data module 100. The housing is configured to be handled by a user to facilitate attachment of the data module 100 to an electrosurgical tool and removal of the data module 100 from the electrosurgical tool. The housing is fluid tight, which may help protect the components housed by the housing from being damaged by liquid and/or gas that the data module 100 may be exposed to before, during, or after the data module's attachment to an electrosurgical tool. The housing includes a front housing 102 and a back housing 104 that are configured to be fixedly attached together. The fixed attachment of the front and back housings 102, 104 facilitates the fluid tight configuration of the housing and helps prevent at least the components fully contained within the housing from being tampered with and/or damaged. In other embodiments, the housing can be a single housing or can include more than two housing parts configured to be fixedly attached together.

Each component of the data module 100 can be housed entirely in the housing or housed partially in the housing. At least some of the data module's components can be housed partially in the housing, so as to be located and/or be accessible from outside the housing, to maximize utility of those component(s), as discussed further below. As in this illustrated embodiment, each of the data module's electronic components (e.g., memory, power source, communication mechanism, etc.) can be housed entirely within the housing to help prevent each of the electronic components from being damaged by fluid and help protect each of the electronic components from being tampered with or otherwise damaged. Non-electronic components of the data module 100 can either be housed entirely in the housing or housed partially in the housing.

The data module 100 also includes a printed circuit board (PCB) 106 configured to mechanically support and electrically connect the data module's electronic components. To facilitate the electrical connections, the PCB 106 can include a bus system, e.g., one or more separate physical buses, communication lines/interfaces, and/or multi-drop or point-to-point connections, connected by appropriate bridges, adapters, and/or controllers.

In this illustrated embodiment, the data module's electronic components include a power source 108, a plurality of lights 110 and a controller 112. The power source 108 is a single power source in this illustrated embodiment, although the power source 108 can include a plurality of power sources in other embodiments. Providing a single power source 108 may help conserve space within the housing to allow for a smaller housing and/or to allow room for more housed components. A single power source 108 can be configured to provide sufficient power because the data module 100 is configured for one-time use with one tool and thus will be in use for a limited amount of time.

Each of the plurality of lights 110 is an LED in this illustrated embodiment. In other embodiments, instead of the four lights 110 a different number of lights and/or a different type of light can be used. Providing a plurality of lights 110 as opposed to a single light, may help ensure that illuminated light is visible to a user of the tool to which the data module 100 is removably attached regardless of a current orientation of the data module 100 relative to the user. Providing a plurality of lights 110, as opposed to a single light, may allow for more detailed information to be provided by light illumination, such as by allowing different ones of the lights 110 to be illuminated at a same time with different combinations of illuminated lights indicating different information, by allowing the lights 110 to be sequentially illuminated such as to show progress, by allowing different ones of the lights 110 to be illuminated in a different color than one or more of the other illuminated lights 110 with different colors and/or different color patterns indicating different information, etc. The lights 110 are configured to provide information to a use of a powered surgical tool to which the data module 100 is removably attached in real time with use of the powered surgical tool in an operative setting, e.g., during performance of a surgical procedure on a patient.

The plurality of the lights 110 is positioned for top and side visibility, as discussed further below. In other embodiments, the light(s) can be positioned for front visibility, bottom visibility, left side visibility, and/or right side visibility.

The controller 112 in this illustrated embodiment includes a memory and a communication mechanism. The controller 112 is a microcontroller in this illustrated embodiment but can be another type of controller, such as a microprocessor or central processing unit (CPU), including programmable general-purpose or special-purpose microprocessors and/or any one of a variety of proprietary or commercially available single or multi-processor systems. In an exemplary embodiment the controller 112 is a single controller, which may help control cost and/or size of the data module 100.

The memory is configured to store data therein. The memory can include storage using, e.g., read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The communication mechanism is configured to communicate data, e.g., data stored in the memory, to an external device and is configured to receive data, e.g. from the external device and/or from a powered surgical tool to which the data module 100 is removably attached, for storage in the memory. In an exemplary embodiment, the communication mechanism is configured to communicate wirelessly using any of a variety of wireless techniques, e.g., Wi-Fi, Near Field communication (NFC), Bluetooth, Bluetooth Low Energy (BLE), cellular communication, radio frequency identification (RFID) communication, etc. The communication mechanism being configured to communicate wirelessly using a passive communication technology, such as NFC or RFID, as the communication interface's only wireless capability or as one of a plurality of wireless capabilities of the communication mechanism (e.g., NFC and BLE, NFC and Bluetooth, RFID and BLE, RFID and Bluetooth, etc.), may allow for data stored at the data module 100, e.g., in the memory, to be retrieved from the data module 100 even if the power source 108 has been deleted of power or lacks sufficient power to allow for communication from the communication mechanism, for example if the power source 108 as a battery has run out of battery power or lacks sufficient battery power to allow for communication from the communication mechanism. Passive communication technology allows a data source to wirelessly receive energy from a data destination, e.g., from an external device. Accordingly, the communication mechanism being configured to communicate using passive communication technology allows the communication mechanism to receive power from the data destination, e.g., from an NFC reader, an RFID reader, or other external device including the appropriate passive communication capability, such that data stored at the data module 100 can be communicated from the communication mechanism using passive communication technology even if the power source 108 has been deleted of power or lacks sufficient power to allow for communication from the mechanism.

The power source 108 may run out of power or have an insufficient power supply for communication from the communication mechanism before all desired data has been retrieved from the data module 100 for any of a variety of reasons. For example, the communication mechanism may be out of range of an external device until after the power source 108 has been depleted of power. For another example, the data module 100 including the power source 108 may have been manufactured long enough ago that the power source 108 was depleted of power before all desired data could be retrieved from the data module 100. For yet another example, the power source 108 may have become damaged and/or otherwise experienced an error preventing the power source 108 from providing power as needed for data to be communicated from the data module 100 to the external device.

The communication mechanism being configured to communicate wirelessly using passive communication technology, as the communication mechanism's only wireless capability or as one of a plurality of wireless capabilities of the communication mechanism (e.g., NFC and BLE, NFC and Bluetooth, RFID and BLE, RFID and Bluetooth, etc.), may allow for data to be stored on the data module 100, e.g., in the memory thereof, as part of the data module's manufacturing process and/or at other time(s) before the data module 100 is removably attached to a powered surgical tool. Passive communication technology allows data to be communicated from an external device, e.g., an NFC reader, an RFID reader, or other external device including the appropriate passive communication capability, to the communication mechanism for storage on the data module 100. The external device can have an app or other program installed thereon configured to facilitate communication with the data module 100.

For example, patient data can be stored on the data module 100 related to a patient with which a powered surgical tool, having the data module 100 removably attached thereto, is to be used. With the data module removably attached to the powered surgical tool, the data regarding the patient can be communicated to the powered surgical tool, e.g., using the communication mechanism, and the powered surgical tool can be configured to use the data to control one or more electronic control parameters of the powered surgical tool, such as a speed or an impact force of the powered surgical tool. The patient data can be anonymous so as to be associated with a particular patient without the patient's identity being indicated by or discernable from the patient data.

For another example, type information can be stored on the data module 100 that identifies one or more types of powered surgical tool to which the data module 100 can be removably attached. The type information can uniquely identify the one or more types of powered surgical tool, such as with an identification code. The powered surgical tool to which the data module is removably attached can be configured to receive the type information from the data module 100 to verify compatibility of the data module 100 with the powered surgical tool and to indicate verified compatibility or unverified compatibility via the lights 110, e.g., one illuminated color to indicate successful verification and another illuminated, different color to indicate failed verification. Alternatively or in addition, the data module 100 can be configured to similarly use the type information to verify compatibility of the data module 100 with a powered surgical tool to which the data module 100 is removably attached. Alternatively or in addition, to the data module 100 and/or a powered surgical tool using the type information to verify compatibility, the data module 100 can be configured to use the type information to determine one or more data parameters relevant to the particular powered surgical tool to which the data module 100 is removably attached. The type information can identify the relevant data parameters for each of the types. The data module 100 can be configured to be removably attached to different types of powered surgical tools, each of which may gather data regarding different parameters. The data module 100, having received identification information from the powered surgical tool that identifies the powered surgical tool, e.g., with an identification code, a serial number, etc., can identify the type of the powered surgical tool based on the identification information and use the type information to identify the relevant data parameter(s) for that type that the data module 100 should receive from the tool and store in the memory.

For yet another example, key data can be stored on the data module 100. The key data includes a number or code that is configured to allow for use of the powered surgical tool to which the data module 100 is removably attached. In such embodiments, the powered surgical tool is configured to be unusable until the key data is received from the data module 100 and verified by the powered surgical tool. In other words, the key data is configured to unlock use of the powered surgical tool. The powered surgical tool to which the data module 100 is removably attached is configured to receive the key data and compare the key data to corresponding key data stored at the powered surgical tool, e.g., in a memory thereof. If the key data from the data module matches the key data stored at the powered surgical tool, the powered surgical tool is unlocked, e.g., a controller of the powered surgical tool allows for further use of the powered surgical tool. The key data stored at the powered surgical tool can include a plurality of numbers or codes, each of which is a valid key that may be received from a data module. Different data modules may thus have different keys (numbers or codes) stored thereon.

Figure 9:
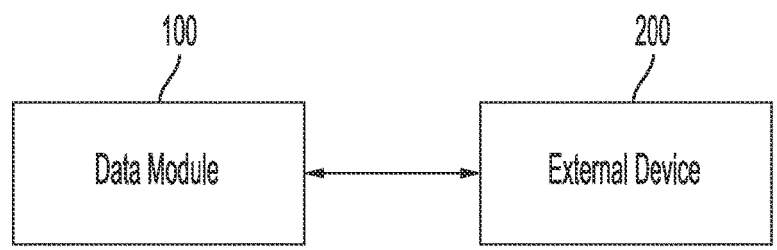
FIG. 9 is a schematic view of the data module of FIG. 1 and an external device configured to communicate with the data module.
Figure 10:
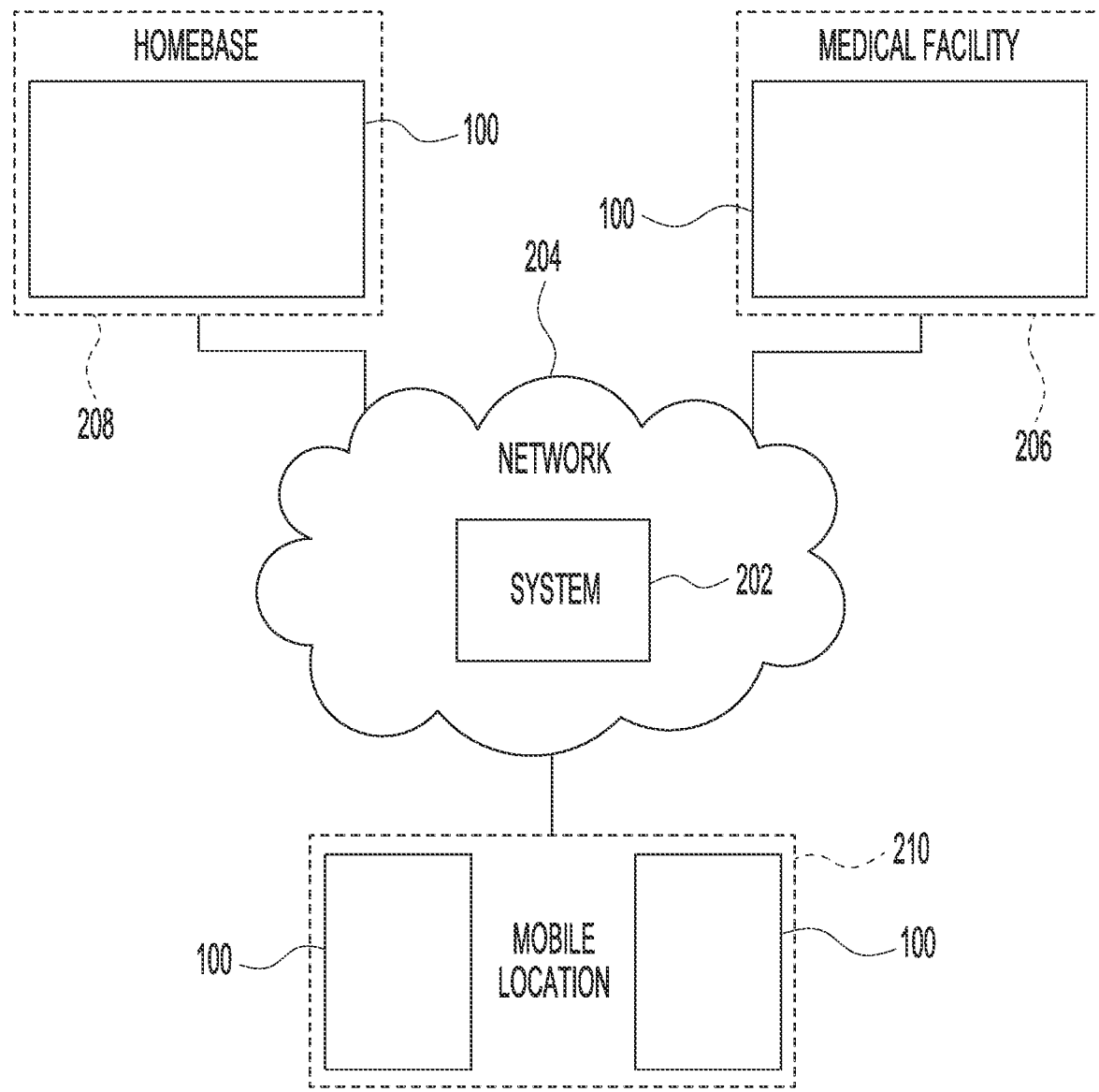
FIG. 10 is a schematic view of a communication network including the data module of FIG. 1.

The communication mechanism of the data module 100 is configured to communicate with an external device 200, as shown in FIG. 9. The communication is wireless in the illustrated embodiment but, in other embodiments, can additionally or alternatively be wired. The external device 200 can be located locally to the data module 100, such as by being in a same room as the data module 100. Alternatively, as shown in FIG. 10, the external device 200 can be located remotely from the data module 100, such as by being in a different facility, different city, different state, etc. from the data module 100. As shown in FIG. 10, the communication mechanism of the data module 100 is configured to communicate with the external device 200, shown as a computer system 202 in FIG. 10, through a communication network 204 from any number of locations where the data module 100 may be located, such as a medical facility 206, e.g., a hospital or other medical care center, a home base 208 (e.g., a manufacturing facility, a distribution center, etc.), or a mobile location 210. Each of a plurality of data modules 100 present at a location can be configured to communicate with the computer system 202, as shown for example in FIG. 10 in which multiple data modules 100 at the mobile location 210 are configured to communicate with the computer system 202. The network 204 can include one or more security features, e.g., encryption, mutual authentication, etc., to help protect unauthorized access to transmitted data and/or to nodes within the network 204.

The external device 200 (computer system 202) can have any of a variety of configurations, as will be appreciated by a person skilled in the art, including components such as a processor, a communication mechanism, a memory, an input/output interface, and a bus system. The external device 200 (computer system 202) can also include any of a variety of other software and/or hardware components, including by way of non-limiting example, operating systems and database management systems. The external device 200 (computer system 202) can be any of a variety of types of computer systems, such as a desktop computer, a workstation, a minicomputer, a laptop computer, a tablet computer, a personal digital assistant (PDA), a mobile phone, a smart watch, etc.

The computer system 1000 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The external device 200 (computer system 202) can also include a web server for generating and/or delivering the web pages to client computer systems. The presented pages and/or streams may allow a user of the external device 200 (computer system 202) to view data received by from the data module 100 and/or analysis of the data as performed by the external device 200 (computer system 202).

Referring again to FIGS. 1-8, the data module 100 also includes a protective cover 114. The protective cover 114 is configured to protect the PCB 106 and any component(s) thereof underlying a plurality of openings 104a formed in the housing, e.g., in the front housing 104. The protective cover 114 is partially housed by the housing. The housing has four openings 104a formed therein in this illustrated embodiment but can include another number, e.g., one, two, three, five, etc. The openings 104a can be in a different location on the housing than in this illustrated embodiment. The protective cover 114 in this illustrated embodiment is transparent, translucent, or otherwise made to allow illumination of light to be visible therethrough from outside the data module 100, such as by the protective cover 114 being a clear or frosted plastic, as one or more lights can be on the PCB 106 and aligned with the openings 104a. Such light(s) are configured to face outward from a powered surgical tool to which the data module 100 is removably attached. The protective cover 114 is thus on the front of the data module 100, thereby allowing light illumination from the one or more lights to be visible at the front of the data module 100.

The data module 100 also includes a support 116 configured to mount to the PCB 106. The support 116 is configured to securely hold the PCB 106 within the housing. In an exemplary embodiment, the support 116 is transparent, translucent, or otherwise made to allow illumination of the plurality of lights 110 to be visible therethrough from outside the data module 100, such as by the support 116 being a clear or frosted plastic. The light support 116 is partially housed by the housing. At least a portion of the support 116 overlying the lights 110 is exposed at an exterior of the data module 100 to facilitate visibility of the illuminated lights 110 through the support 116.

The support 116 extends completely along a top of the data module 100 and partially along each side of the data module 100 from the top of the data module 100. The support 116 thus allows light 110 illumination to be visible at the top and each side (left and right) of the data module 100. Light 110 illumination being simultaneously visible at the top and side of the data module 100 may facilitate user viewing of the illumination regardless of the user's current perspective of the data module 100.

The data module 100 includes a handle 120 configured to be held by a user to facilitate mating of the data module to a powered surgical tool and removal of the data module from the powered surgical tool. The handle 120 is defined by the housing (the back housing 104 in this illustrated embodiment). The handle 120 protrudes forward so as to be accessible to a user at a front of the data module 100 during attachment of the data module 100 to a powered surgical tool and during removal of the data module 100 from the powered surgical tool.

The data module 100 is configured to be removably attached to a powered surgical tool by being seated in a slot of the powered surgical tool. The data module 100 is configured to slide bottom-side first into the slot, e.g., with a user holding the handle 120 and moving the data module 100 down through the slot. The data module 100 includes opposed side shelves 118 that are configured to seat on corresponding opposed side shelves of the powered surgical tool when the data module 100 is fully seated in the slot. A bottom surface 120 of each of the data module's side shelves can include a mating element in the form of a protrusion, configured to releasably mate with a mating feature in the form of a depression formed in a top surface of the corresponding tool side shelf, and/or the bottom surface 120 of each of the data module's side shelves can include a mating element in the form of a depression formed therein that is configured to releasably mat with a mating feature in the form of a protrusion extending from the top surface of the corresponding tool side shelf. The mating element/mating feature pairs can help align the data module 100 and the powered surgical tool. The mating of the element/mating feature pairs can cause an audible sound, e.g., a click or pop as a protrusion fits into depression, which can help confirm to a user that the data module 100 has been properly removably attached to the powered surgical tool. The data module 100 is configured to be removed from the powered surgical tool by being removed from the slot by being up, e.g., with a user holding the handle 120 and moving the data module 100 up through the slot until the data module 100 is released completely from the powered surgical tool.

FIGS. 11-17 illustrate another embodiment of a data module 300 configured to removably attach to a powered surgical tool such as an electrosurgical tool. The data module 300 is generally configured and used similar to the data module 100 of FIGS. 1-10, e.g., is configured to be disposable and includes a housing 302, a light cover 304, a support 306, a handle 308, a power source, a plurality of lights, and a controller that includes a memory and a communication mechanism. The power source, the plurality of lights, and the controller are obscured in FIGS. 11-17. The data module 300 includes eight lights similar to the data module 100 but, as mentioned above with respect to the data module 100 of FIGS. 1-10, can include another number of lights. The data module 300 of FIGS. 11-17 has a two-piece housing similar to the housing of the data module 100 of FIGS. 1-10.

Figure 11:
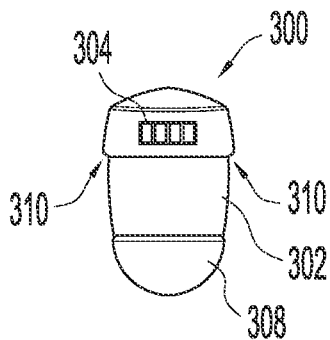
FIG. 11 is a front view of another embodiment of a data module.
Figure 12:
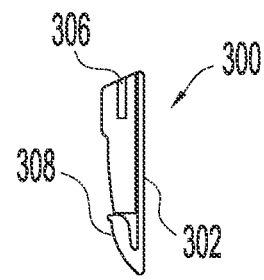
FIG. 12 is a side view of the data module of FIG. 11.

FIGS. 11 and 12 show the data module 300 as a stand-alone element, and FIGS. 13-17 show the data module 300 removably attached to one embodiment of a powered surgical tool 400. The data module 300 is configured to be removably attached to and removed from the powered surgical tool 400 similar to that discussed above regarding the data module 100 of FIGS. 1-10. FIGS. 13-17 thus show the data module 300 removably seated in a slot (obscured in FIGS. 13-17) of the powered surgical tool 400. The data module 300 includes opposed side shelves 310 configured to seat on corresponding side shelves 402 of the powered surgical tool 400, similar to the side shelves 118 discussed above. A bottom surface of the data module's shelves 310 can include a mating element, and a corresponding top surface of the powered surgical tool's shelves 402 can include a mating feature, similar to the mating element and mating feature discussed above.

The powered surgical tool 400 in this illustrated embodiment is an electrosurgical tool in the form of an orthopedic impactor. However, as mentioned above, the data module 300 can be removably attached to another type of powered surgical tool. Various exemplary embodiments of orthopedic impactors are further described in U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014, which are hereby incorporated by reference in their entirety.

FIGS. 13-17 also show the lights 110 of the data module 300 illuminated, each illumination being indicative of a different condition of the tool 400. The colors of the light in FIGS. 13-17 are examples. Other colors may be used.

Figure 13:
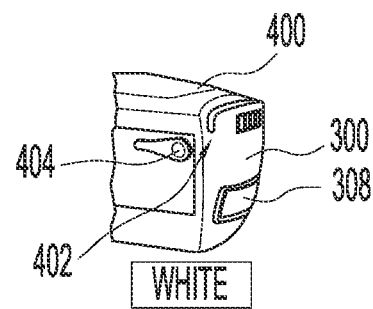
FIG. 13 is a perspective view of the data module of FIG. 11 attached to one embodiment of an electrosurgical tool and with a light of the data module illuminated in a first color.
Figure 14:
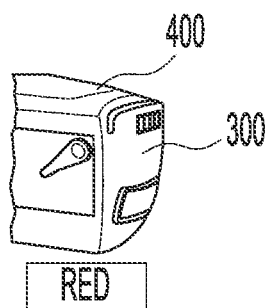
FIG. 14 is another perspective view of the data module and the electrosurgical tool of FIG. 13 with the light of the data module illuminated in a second color and with the electrosurgical tool in an intermediate energy mode.
Figure 15:
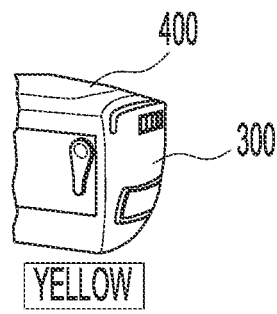
FIG. 15 is yet another perspective view of the data module and the electrosurgical tool of FIG. 13 with the light of the data module illuminated in a third color.

The light in FIGS. 13-15 indicates an energy mode of the tool 400. FIG. 13 illustrates the lights 110 illuminated in a first color, e.g., white, to indicate a low energy mode of the tool 400. An energy control lever 404 of the tool 400 is in a position corresponding to the low energy mode. FIG. 14 illustrates the lights 110 illuminated in a second, different color, e.g., red, to indicate an intermediate energy mode of the tool 400 that is higher energy than the low energy mode. The energy control lever 404 of the tool 400 is in a position corresponding to the intermediate energy mode. FIG. 15 illustrates the lights 110 illuminated in a third color, e.g., yellow, to indicate a high energy mode of the tool 400 that is higher energy than the intermediate energy mode. The energy control lever 404 of the tool 400 is in a position corresponding to the high energy mode.

Figure 16:
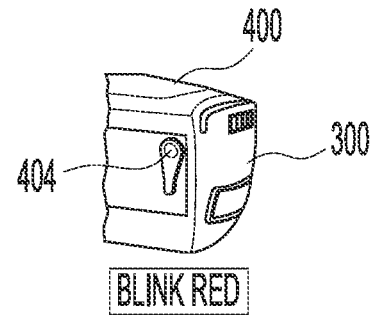
FIG. 16 is still another perspective view of the data module and the electrosurgical tool of FIG. 13 with the light of the data module illuminated and blinking in the second color.
Figure 17:
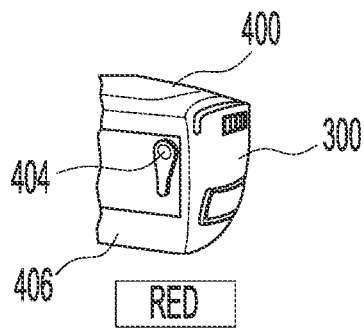
FIG. 17 is another perspective view of the data module and the electrosurgical tool of FIG. 13 with the light of the data module illuminated and blinking in the second color and with the electrosurgical tool in a high energy mode.

The light in FIGS. 16 and 17 indicates an operational status of the tool 400. FIG. 16 illustrates the lights 110 illuminated and blinking to indicate a temperature warning, e.g., that a temperature sensed by a temperature sensor (not shown) of the tool 400 has sensed a temperature above a predetermined maximum threshold pressure. In response to seeing the light illuminated and blinking, a user of the tool 400 can stop energy application to allow for temperature cooling. As shown in FIG. 16, the tool 400 is in the high energy mode with the temperature warning being provided. FIG. 17 illustrates the lights 110 illuminated in red to indicate a handpiece error, e.g., that an error has occurred at a handpiece 406 of the tool 400 such as a jammed energy application trigger, a jammed energy mode lever 404, or other error.

Other conditions that can be shown with the lights 110 include an indication of a charge level of the data module's power source 108. For example, in response to the data module 100 being removably attached to a powered surgical tool, the powered surgical tool can cause the lights 110 to illuminate (blinking or solid) either in a first color, e.g., white, to indicate that the power source 108 has at least a minimum predetermined charge level, or in a second color, e.g., red, to indicate that the power source 108 does not have at least the minimum predetermined charge level. The minimum predetermined charge level can correspond to a typical maximum amount of time of a surgical procedure using the powered surgical tool, e.g., two hours, three hours, four hours, etc. The second color being shown upon attachment of the data module 100 to the powered surgical tool can thus indicate to a user of the powered surgical tool that the data module 100 should be removed and replaced with another data module because the data module 100 may lack a sufficient power supply for use of the powered surgical tool.

Instead of or in addition to the condition of the tool 400 being shown with the top/side light as discussed above, the condition of the tool 400 can be shown with the front light.

Figure 18:
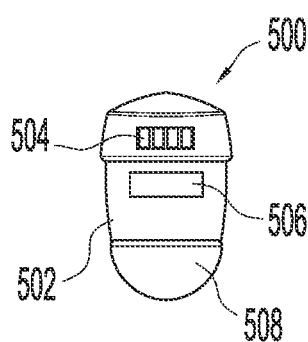
FIG. 18 is a front view of yet another embodiment of a data module.

FIG. 18 illustrates another embodiment of a data module 500 configured to removably attach to a powered surgical tool such as an electrosurgical tool. The data module 500 is generally configured and used similar to the data module 100 of FIGS. 1-10, e.g., is configured to be disposable and includes a housing 502, a light cover 504, a handle 508, a support, a power source, a plurality of lights, and a controller that includes a memory and a communication mechanism. The power source, the plurality of lights, and the controller are obscured in FIG. 18. The data module 500 includes eight lights similar to the data module 100 but, as mentioned above with respect to the data module 100 of FIGS. 1-10, can include another number of lights. The data module 500 of FIG. 18 has a two-piece housing similar to the housing of the data module 100 of FIGS. 1-10. In this illustrated embodiment, the data module 500 includes a display 506, such as a graphical user interface (GUI), liquid crystal display (LCD), etc., configured to show information thereon to a user. The information shown on the display 506 can correspond to the information being indicated by the illumination of the lights but be provided in text and/or graphic form. The lights and the display 506 can thus provide redundancy and help ensure that a user of the powered surgical tool to which the data module 500 is attached can see information via the lights, via the display, or via the display 506 and the lights. The powered surgical tool to which the data module 500 is attached can be configured to control the display 506 similar to the tool's control of the lights. The display 506 is on a front of the data module 500 in this illustrated embodiment, which is a same side as the lights, but the display 506 can be on another surface of the data module 500. The data module 500 includes a single display 506 in this illustrated embodiment but can include more than one display, which may allow different information to be shown on different ones of the displays and/or for different surfaces (e.g., top and front, front and one side, front and two opposed sides, etc.) to have a display thereon to help allow a user to see at least one display regardless of a user's current vantage point of the data module 500.

Figure 19:
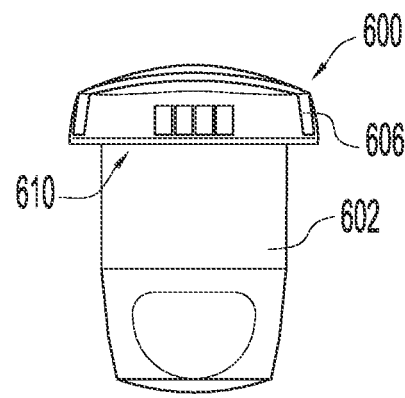
FIG. 19 is a back view of still another embodiment of a data module.
Figure 20:
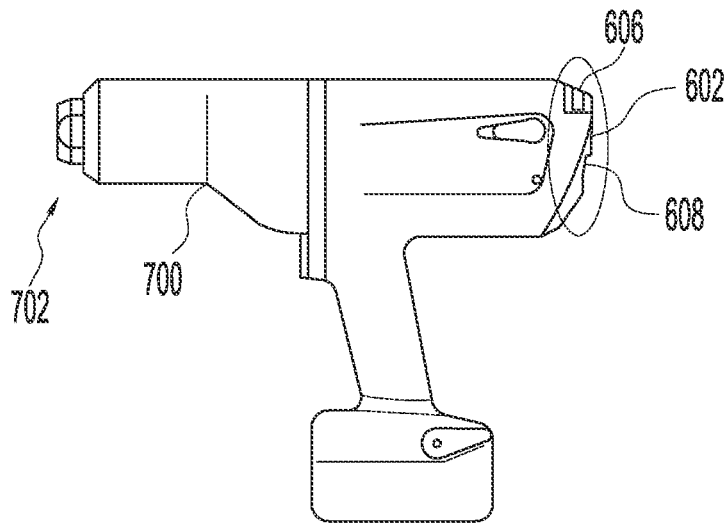
FIG. 20 is a perspective view of the data module of FIG. 19 attached to another embodiment of an electrosurgical tool.
Figure 21:
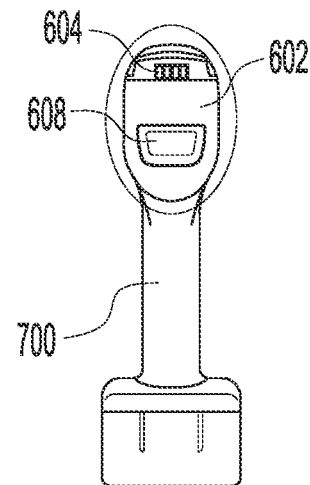
FIG. 21 is a back view of the data module and the electrosurgical tool of FIG. 20.

FIGS. 19-21 illustrate another embodiment of a data module 600 configured to removably attach to a powered surgical tool such as an electrosurgical tool. The data module 600 is generally configured and used similar to the data module 100 of FIGS. 1-10, e.g., is configured to be disposable and includes a housing 602, a light cover 604, a support 606, a handle 608, a power source, a plurality of lights, and a controller that includes a memory and a communication mechanism. The power source, the plurality of lights, and the controller are obscured in FIGS. 19-21. The data module 600 includes eight lights similar to the data module 100 but, as mentioned above with respect to the data module 100 of FIGS. 1-10, can include another number of lights. The housing 602 is a two-piece housing similar to the housing of the data module 100 of FIGS. 1-8.

FIG. 19 shows the data module 600 as a standalone element, and FIGS. 20 and 21 show the data module 600 removably attached to one embodiment of a powered surgical tool 700. The data module 600 is configured to be removably attached to and removed from the powered surgical tool 600 similar to that discussed above regarding the data module 100 of FIGS. 1-10. FIGS. 20 and 21 thus show the data module 600 removably seated in a slot (obscured in FIGS. 20 and 21) of the powered surgical tool 700. In this illustrated embodiment, instead of having opposed side shelves configured to seat on a surface of a powered surgical tool, the data module 600 includes a single shelf 610 extending along a back of the data module 600 and having a bottom surface configured to seat on a top surface (obscured in FIGS. 20 and 21) of the powered surgical tool 700. The bottom surface of the shelf 610 can include a mating element, and the corresponding top surface of the powered surgical tool 600 can include a mating feature, similar to the mating element and mating feature discussed above.

The powered surgical tool 700 in this illustrated embodiment is an electrosurgical tool in the form of an orthopedic impactor. However, as mentioned above, the data module 500 can be removably attached to another type of powered surgical tool. An adapter (not shown) and an end effector (or surgical implement) (not shown) are configured to be removably attached to the powered surgical tool 700 at a distal or forward end 702 of the tool 700. In some embodiments, the end effector is non-removably attached to the orthopedic impactor. Various exemplary embodiments of orthopedic impactors, as well as adapters and end effectors, are further described in previously mentioned U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014.

In some embodiments, a data module configured to removably attach to a powered surgical tool, such as an electrosurgical tool, includes data storage and communication capability but does not include a power source or any lights. In such embodiments, the data module is configured to allow data stored on the data module to be communicated to a powered surgical tool to which the data module is removably attached. In general, such a data module is less complex and has fewer components than the data modules 100, 300, 500, 600 discussed above. The data module can thus have a lower cost. In an exemplary embodiment, the data module is configured to be disposable.

The data module's communication mechanism in such embodiments is configured to communicate wirelessly using a passive communication technology, such as NFC or RFID, such that attachment of the data module to the powered surgical tool allows data to be communicated from the data module to the powered surgical tool that includes corresponding communication technology capability. The powered surgical tool can thus receive data from the data module that the powered surgical tool can use in various ways, as discussed above. The data stored on the data module can be different types of data in different embodiments. In one exemplary embodiment, the data stored on the data module includes key data. In another exemplary embodiment, the data stored on the data module includes patient data. In yet another exemplary embodiment, the data stored on the data module includes key data and patient data.

The data module in such embodiments can be configured to only transmit information, e.g., one-way communication with data communicated to a powered surgical tool to which the data module is removably attached, or can be configured to transmit and receive information, e.g., two-way communication between the data module and a powered surgical tool to which the data module is removably attached. In such embodiments with two-way communication, the data module is configured to store data received from the powered surgical tool for later communication to an external device. The data modules 100, 300, 500, 600 discussed above are configured for two-way communication.

Figure 22:
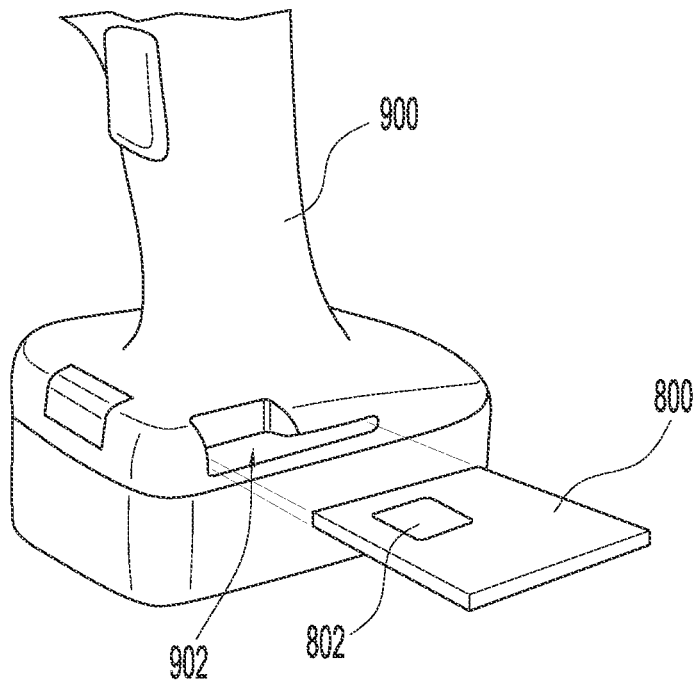
FIG. 22 is a perspective view of another embodiment of a data module attachable to another embodiment of an electrosurgical tool.

FIG. 22 illustrates another embodiment of a data module 800 configured to removably attach to a powered surgical tool, such as an electrosurgical tool. The data module 800 in this illustrated embodiment includes data storage and communication capability but does not include a power source or any lights. The data module 800 in this illustrated embodiment includes an RFID tag 802 configured to store data and to passively communicate using RFID. The data module 800 in this illustrated embodiment is in the form of a card that has the RFID tag 802 embedded therein or otherwise fixedly attached thereto. The data module 800 is configured to be disposable.

FIG. 22 shows the data module 800 being removably attachable to a powered surgical tool 900 in the form of an orthopedic impactor. However, as mentioned above, the data module 800 can be removably attached to another type of powered surgical tool. Various exemplary embodiments of orthopedic impactors are further described in previously mentioned U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014. The powered surgical tool 900 includes a slot 902 formed therein that is configured to releasably receive the data module 800 therein.

In some embodiments, a data module configured to removably attach to a powered surgical tool, such as an electrosurgical tool, is configured as a key, similar to use of the key data discussed above, but does not includes data storage, communication capability, a power source, or any lights. In general, such a data module is less complex and has fewer components than the data modules 100, 300, 500, 600, 800 discussed above. The data module can thus have a lower cost. In an exemplary embodiment, the data module is configured to be disposable.

The data module in such embodiments can include magnetic sensing technology, such as a Hall sensor, a reed switch, or other technology, configured to serve as the key. A powered surgical tool configured to removably attached to such a data module is configured to generate or otherwise provide a magnetic field configured to interact with the magnetic sensing technology of the data module. In this way, when the data module is removably attached, the powered surgical tool can determine that the data module has been attached thereto, thereby unlocking the powered surgical tool for use.

Figure 23:
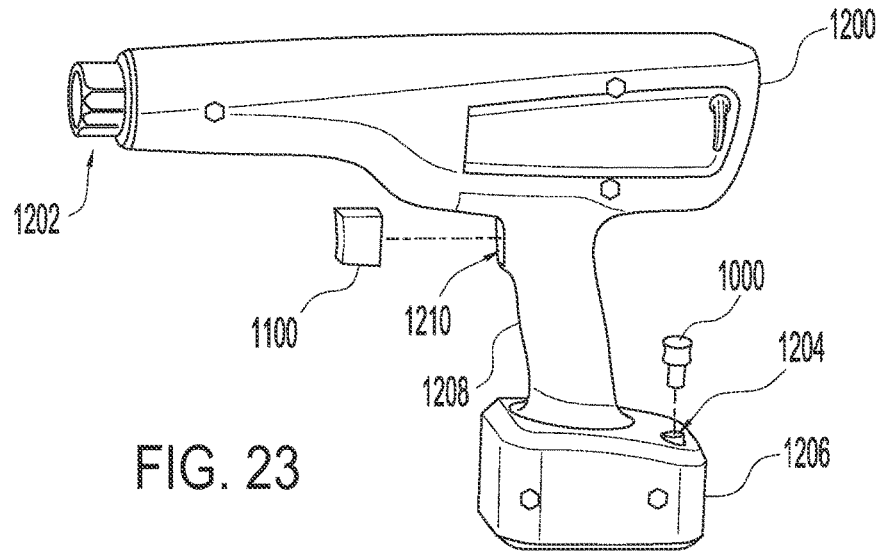
FIG. 23 is a perspective view of two embodiments of a data module attachable to another embodiment of an electrosurgical tool.

FIG. 23 illustrates two other embodiments of data modules 1000, 1100 configured to removably attach to a powered surgical tool, such as an electrosurgical tool. The data modules 1000, 1100 in this illustrated embodiment are each configured as a key and do not include data storage, communication capability, a power source, or any lights. The data modules 1000, 1100 are each configured to be disposable.

FIG. 23 shows a powered surgical tool 1200 that is configured to removably attach to each of the data modules 1000, 1100. The tool 1200 is thus configured to be unusable until each of the two keys from the data modules 1000, 1100 is verified. In other embodiments, a powered surgical tool can be configured to removably attach to only one of the data modules 1000, 1100 and thus be unlocked when only a single key is verified.

The powered surgical tool 1200 in this illustrated embodiment is an electrosurgical tool in the form of an orthopedic impactor. However, as mentioned above, the data modules 1000, 1100 can be removably attached to another type of powered surgical tool. An adapter (not shown) and an end effector (or surgical implement) (not shown) are configured to be removably attached to the powered surgical tool 1200 at a distal or forward end 1202 of the tool 1200. In some embodiments, the end effector is non-removably attached to the orthopedic impactor. Various exemplary embodiments of orthopedic impactors, as well as adapters and end effectors, are further described in previously mentioned U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014.

A first one of the data modules 1000 is configured as a dongle. The powered surgical tool 1200 includes a port 1204 configured to releasably seat the data module 1000 therein. In response to the data module 1000 being seated in the port 1204, the powered surgical tool 1200 is configured to unlock. The port 1204 is formed in a top surface of a base 1206 of a handpiece 1208 of the powered surgical tool 1200 in this illustrated embodiment but can be formed elsewhere in the base 1206, in the handpiece 1208, or elsewhere on the tool 1200. The data module 1000 as a dongle does not serve any function of the tool 1200 except an unlocking function.

A second one of the data modules 1100 is configured as a trigger of the powered surgical tool 1200. The powered surgical tool 1200 includes a cavity 1210 configured to releasably seat the data module 1100 therein. In response to the data module 1100 being seated in the cavity 1210, the powered surgical tool 1200 is configured to unlock. The port cavity 1210 is formed in the handpiece 1208 of the powered surgical tool 1200 in this illustrated embodiment but can be formed elsewhere, depending on a configuration of the powered surgical tool 1200 to allow for trigger actuation. The data module 1100 as a trigger serves a function of the powered surgical tool 1200 in addition to an unlocking function. The data module 1100 as a trigger removably attached to the powered surgical tool 1200 is configured to be actuated to cause impacting. The data module 1100 is thus configured to provide two levels of security for the powered surgical tool 1200 with the powered surgical tool 1200 being unlocked by the data module 1100 using the magnetic sensing technology and the powered surgical tool 1200 being unable to be actuated until the data module 1100 is removably attached to the powered surgical tool 1200 because the powered surgical tool 1200 lacks an actuator for impacting until the data module 1100 is removably attached to the powered surgical tool 1200.

Figure 24:
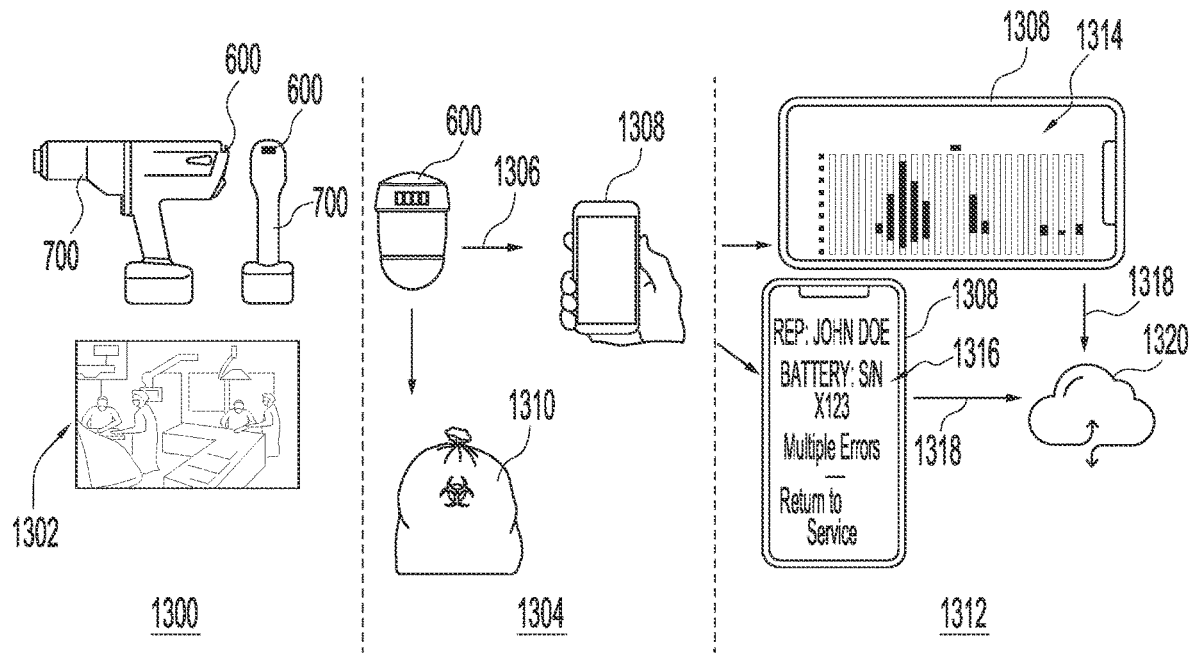
FIG. 24 illustrates stages of a method of using the data module and the electrosurgical tool of FIGS. 20 and 21.

FIG. 24 illustrates one embodiment of a method of using a data module. The method is described with respect to the data module 600 of FIGS. 19-21 and the electrosurgical tool 700 of FIGS. 20 and 21 but can be similarly performed with other embodiments of data modules and powered surgical tools described herein.

The method of FIG. 24 includes three stages. A first stage 1300 of the method is a use stage in which the data module 600 is used with the electrosurgical tool 700 during performance of a surgical procedure on a patient, which is represented in FIG. 24 as an operating room setting 1302. The data module 600 is removably attached to the electrosurgical tool 700 as discussed above and then the electrosurgical tool 700 is used per its typical use in the surgical procedure.

In the first stage 1300 with the data module 600 removably attached to the electrosurgical tool 700, information can be communicated from the electrosurgical tool 700 to the data module 600, e.g., from a communication mechanism of the electrosurgical tool 700 to the communication mechanism of the data module 600, and stored at the data module 600, e.g., in the memory thereof. The data module 600 can thus receive and store data in real time with use of the electrosurgical tool 700 in the surgical procedure. A controller of the electrosurgical tool 700 can control the information communication to the data module 600. Various types of information can be communicated to and stored at the data module 600.

One example of information that can be communicated to and stored at the data module 600 includes operational information regarding operation of the electrosurgical tool 700 during the surgical procedure. Examples of operational information include information related to impaction, such as a number of impactions provided by the electrosurgical tool 700 (which, as mentioned above, is an orthopedic impactor in this illustrated embodiment), a direction of each of the electrosurgical tool's impacts (e.g., forward or reverse), a force of each of the electrosurgical tool's impacts (which can either be a force value or a force indicator such as high or low), an energy mode in which an impact was delivered (e.g., low energy mode or high energy mode), whether an impact provided by the electrosurgical tool is a single fire impact or one of a plurality of continuous fire impacts, and other operational information related to impaction. For example, the electrosurgical tool 700 can communicate to the data module 600 during the course of the first stage 1300 that seventy-two high continuous impacts were provided, that twelve high single impacts were provided, that one hundred twenty-seven low continuous impacts were provided, that eleven low single impacts were provided, that twenty-eight reverse continuous impacts were provided, that six reverse continuous impacts were provided, etc. Other examples of operational information may not be related to impaction and thus may not be operational information limited to use with orthopedic impactors, such as a number of times the electrosurgical tool's trigger is actuated, a speed of a motor driving the electrosurgical tool (e.g., a motor driving the tool's impacting, drilling, sawing, etc.), a current of a motor driving the electrosurgical tool (e.g., a motor driving the tool's impacting, drilling, sawing, etc.), and other operational information.

Another example of information that can be communicated to and stored at the data module 600 includes timing information regarding various time parameters related to the electrosurgical tool 700. Examples of timing information include an amount of time elapsed between attachment of the data module 600 to the electrosurgical tool 700 and removal of the data module 600 from the electrosurgical tool 700; an amount of time elapsed between attachment of the data module 600 to the electrosurgical tool 700 and communication of data from the data module 600 to an external device; an amount of time elapsed between removal of the data module 600 from the electrosurgical tool 700 and communication of data from the data module 600 to an external device; an amount of time elapsed between attachment of the data module 600 to the electrosurgical tool 700 and first actuation of the electrosurgical tool 700 in the surgical procedure; an amount of time elapsed between a first actuation of the electrosurgical tool 700 in the surgical procedure and a last actuation of the electrosurgical tool 700 in the surgical procedure; a time of each actuation of the electrosurgical tool 700 in the surgical procedure; a length of time impacting, drilling, sawing, etc. occurred in response to a trigger actuation; and other timing information. For example, the electrosurgical tool 700 can communicate to the data module 600 during the course of the first stage 1300 that twenty-nine minutes elapsed between attachment of the data module 600 to the electrosurgical tool 700 and communication of data from the data module 600 to an external device, that nineteen minutes elapsed between a first actuation of the electrosurgical tool 700 in the surgical procedure and a last actuation of the electrosurgical tool 700 in the surgical procedure, that in response to a trigger actuation two hundred fifty-six impactions occurred at six impactions per second (for a total of 42.6 seconds of impactions), etc.

Another example of information that can be communicated to and stored at the data module 600 includes error information regarding any errors that occurred during use of the electrosurgical tool 700. Examples of error information include whether a temperature warning was issued, whether the electrosurgical tool 700 stopped functioning, whether a voltage error occurred, whether a current error occurred, and other error information. The data module 600 receiving any error information is indicative of maintenance of the electrosurgical tool 700 being needed or at least evaluated as being needed or not depending on human review of the indicated error. For example, the electrosurgical tool 700 can communicate to the data module 600 during the course of the first stage 1300 that current of a motor of the electrosurgical tool 700 exceeded a predetermined threshold current.

Another example of information that can be communicated to and stored at the data module 600 includes power information regarding a power source of the electrosurgical tool 700. Examples of power information include an amount of power used by the electrosurgical tool's power source during the surgical procedure, identification information (e.g., serial number, lot number, etc.) that identifies the electrosurgical tool's power source, and other power information. Power information may indicate that maintenance of the electrosurgical tool 700 is needed, such as if the electrosurgical tool's power source is rechargeable and in each of a plurality of uses of the electrosurgical tool 700 the power source is using more power per use than expected, if electrosurgical tool's power source ran out of power during the surgical procedure (e.g., 100% power used by the electrosurgical tool's power source during the surgical procedure), etc.

Another example of information that can be communicated to and stored at the data module 600 includes identification information that identifies the electrosurgical tool 700. Examples of identification information include a unique identifier (e.g., a serial number, etc.) that uniquely identifies the electrosurgical tool 700, a batch identifier (e.g., a lot number, a batch code, etc.) that identifies a manufacturing batch of the electrosurgical tool, a manufacturer identifier (e.g., a number, a code, a name, etc.) that identifies a brand or manufacturer of the electrosurgical tool 700, an owner identifier (e.g., a number, a code, a name, etc.) that identifies an owner or purchaser of the electrosurgical tool 700, and other identification information. Identification information can facilitate analysis by an external device that receives the identification information and any other information from the data module 600 by allowing the external device to associate the analysis with a particular tool, batch, manufacturer, owner, etc. and thus identify issues with a particular tool, batch, manufacturer, owner, etc. through analysis of data received from a plurality of data modules.

A second stage 1304 of the method that follows the first stage 1300 is a processing stage in which the data module 600 transmits 1306 data to an external device 1308 and, after the transmission 1306, the data module 600 is disposed. The external device 1308 is a mobile phone in this illustrated embodiment and has an app installed thereon to manage the data received from the data module 600 (and to manage data, such as patient data, sent to the data module 600 before the data module's removable attachment to the electrosurgical tool 700), but as mentioned above, other external devices can be used. The disposal of the data module 600 is represented in FIG. 24 with a biohazard waste disposal bag 1310, but as mentioned above, disposal of a data module 600 can include waste disposal and/or recycling.

The data module 600 is not attached to the electrosurgical tool 700 in the second stage 1304. The data module 600 is thus not attached to the electrosurgical tool 700 when the data is transmitted 1306 to the external device 1308 and when the data module 600 is disposed. The data module 600 can be removed from the electrosurgical tool 700 before or after the electrosurgical tool 700 leaves the operating room setting 1302. However, in other embodiments, the data module 600 can be attached to the electrosurgical tool 700 when the data is transmitted 1306 to the external device 1308. For example, the data module 600 can be configured to begin attempting to transmit 1306 data after a predetermined period of time has elapsed since the data module 600 was attached to the electrosurgical tool 700, e.g., by the data module 600 including a timer and a controller configured to cause the data module's communication module to begin data transmission 1306 attempts after the controller determines based on data from the timer that the predetermined period of time has elapsed. In such a case, the data module 600 may or may not be attached to the electrosurgical tool 700 when the data module 600 begins attempting to transmit 1306 data. The predetermined period of time can correspond to a typical maximum amount of time of a surgical procedure using the powered surgical tool, e.g., two hours, three hours, four hours, etc. For another example, the data module 600 can be configured to begin transmitting 1306 data to the external device 1308 in response to the external device 1308 being in an effective communication range of the data module's communication mechanism. In such a case, the data module 600 may or may not be attached to the electrosurgical tool 700 when the data module 600 begins transmitting 1306 data to the external device 1308. For another example, the data module 600 can be configured to begin transmitting 1306 data to the external device 1308 in response to receiving a request for data from the external device 1308. In such a case, the data module 600 may or may not be attached to the electrosurgical tool 700 when the data module 600 begins transmitting 1306 data to the external device 1308.

As mentioned above, the external device 1308 can transmit data, such as patient data and/or other data, to the data module 600 before the data module 600 is removably attached to the electrosurgical tool 700. The data module 600 can thus have relevant data stored thereon for use of the electrosurgical tool 700 prior to the data module's attachment to the electrosurgical tool 700.

A third stage 1312 of the method that follows the second stage 1304 is an analysis stage in which data from the data module 600 is shown on the external device 1308, e.g., displayed on the external device's screen via an app installed on the external device 1308, displayed on the external device's screen via a web page accessible using the external device 1308, etc. For example, the external device 1308 is shown in FIG. 24 displaying a graph 1314 operational information over time. In this illustrated embodiment, the graph 1314 shows when a particular number of forward impacts were delivered by the electrosurgical tool 700, when a particular number of reverse impacts were delivered by the electrosurgical tool 700, when the electrosurgical tool 700 operated in high energy mode, and when the electrosurgical tool 700 operated in low energy mode. For another example, the external device 1308 is shown in FIG. 24 displaying text 1316 reflecting power information. In this illustrated embodiment, the text 1316 includes a serial number of the electrosurgical tool's power source (which includes a battery in this illustrated embodiment), an indication that multiple errors with the power source occurred during use of the electrosurgical tool 700 with the data module 600 attached thereto, and a recommendation that the electrosurgical tool 700 be returned for service (maintenance). The text 1316 also includes a name of a representative for the company responsible for the electrosurgical tool 700, which helps a user reading the text 1316 know who to contact with any questions.

The external device 1308 can be configured to perform analysis of the data received from the data module 600. Alternatively or in addition, the external device 1308 can be configured to transmit 1318 the data received from the data module 600 to a cloud computer system 1320 for analysis. The cloud computer system 1320 can be configured to aggregate data from a plurality of data modules, including the data module 600, to allow for analysis of multiple data sets from multiple data modules related to multiple electrosurgical tools. The cloud computer system 1320 may thus be able to identify trends by analyzing multiple sets of data.

As mentioned above, the temperatures, moisture levels, and pressures associated with sterilization techniques for sterilizing surgical tools can damage some electronic components such as LEDs (and other types of lights) and rechargeable batteries. During sterilization, temperatures may reach, for example, about 132° C. for several minutes in a pre-vacuum sterilizer or, for another example, about 121° C. for thirty minutes or longer in a gravity displacement sterilizer. A person skilled in the art will appreciate that a value may not be precisely at a value but nevertheless be considered to be about that value for any of a variety of reasons, such as manufacturing tolerances and sensitivity of measurement equipment. Examples of sterilization techniques include autoclaving, beta or gamma radiation, ethylene oxide, steam, and a liquid bath (e.g., cold soak). An exemplary embodiment of sterilizing a surgical tool including internal circuitry is described in U.S. Pat. No. 8,114,345 entitled "System And Method Of Sterilizing An Implantable Medical Device" issued Feb. 14, 2012, which is hereby incorporated by reference in its entirety.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
   an electrosurgical tool including a controller; and
   a data module configured to be removably attached to the electrosurgical tool, the data module including a light, a memory, and a communication mechanism;
   wherein, with the data module removably attached to the electrosurgical tool:

the controller of the electrosurgical tool is configured to control illumination of the light to indicate a condition of the electrosurgical tool, and the data module is configured to receive information from the electrosurgical tool regarding the electrosurgical tool and to store the received information in the memory; and the communication mechanism of the data module is configured to communicate data stored in the memory to an external device.

2. The system of claim 1, wherein the memory is configured to store therein data regarding a patient with which the electrosurgical tool is to be used; and the controller of the electrosurgical tool is configured to adjust a setting of the electrosurgical tool based on the data regarding the patient.

3. The system of claim 1, wherein the information received from the electrosurgical tool includes identification information that identifies the electrosurgical tool; and the information received from the electrosurgical tool includes tool information retrieved from the electrosurgical tool based on the received identification information.

4. The system of claim 1, wherein the information received from the electrosurgical tool includes data regarding operation of the electrosurgical tool in real time with use of the electrosurgical tool on a patient.

5. The system of claim 1, wherein the information received from the electrosurgical tool includes serial data that uniquely identifies the electrosurgical tool.

6. The system of claim 1, wherein the condition is one of a plurality of possible conditions of the electrosurgical tool; and the illumination of the light is different based on the condition being indicated.

7. The system of claim 6, wherein the illumination of the light is different in at least one of color and whether the light is blinking or continuously illuminated; and the plurality of conditions include at least two of temperature, status of a power source of the electrosurgical tool, an energy mode of the electrosurgical tool, and operational status of the electrosurgical tool.

8. The system of claim 1, wherein the condition is selected from the group consisting of temperature, status of a power source of the electrosurgical tool, an energy mode of the electrosurgical tool, and operational status of the electrosurgical tool.

9. The system of claim 1, wherein the electrosurgical tool includes a slot configured to releasably seat the data module therein.

10. The system of claim 1, wherein the electrosurgical tool includes a mating feature; and the data module includes a mating element configured to releasably mate with the mating feature to removably attach the data module and the electrosurgical tool.

11. The system of claim 1, wherein the electrosurgical tool is configured to be sterilized and reused; and the light is configured to not be operational if sterilized.

12. The system of claim 1, wherein the data module includes a housing that houses the light, the memory, and the communication mechanism.

13. The system of claim 1, wherein the electrosurgical tool is one of an orthopedic impactor, a surgical drill, and a surgical reciprocating saw.

14. The system of claim 1, wherein the data module is configured to be removably attached to the electrosurgical tool by being mechanically seated in a slot formed in the electrosurgical tool.

15. The system of claim 1, wherein the electrosurgical tool includes a mating feature; and the data module includes a mating element configured to be removably attached to the electrosurgical tool by the mating element being mechanically attached to the mating feature.

16. The system of claim 1, wherein the electrosurgical tool includes a handpiece configured to be handheld, the controller is disposed in the handpiece, and the data module is configured to be removably attached to the handpiece of the electrosurgical tool.

17. A surgical system, comprising:
a disposable housing configured to be removably attached to an electrosurgical tool;
a light configured to illuminate to indicate a condition of the electrosurgical tool to which the housing is removably attached;
a memory configured to store data therein received from the electrosurgical tool regarding use of the electrosurgical tool to which the housing is removably attached; and
a communication mechanism configured to communicate the data stored in the memory to an external device.

18. The system of claim 17, wherein, with the housing removably attached to the electrosurgical tool, the illumination of the light is configured to be controlled by the electrosurgical tool.

19. The system of claim 17, wherein the condition is one of a plurality of possible conditions of the electrosurgical tool;
the plurality of conditions include at least two of temperature, status of a power source of the electrosurgical tool, an energy mode of the electrosurgical tool, and operational status of the electrosurgical tool;
the illumination of the light is different based on the condition being indicated; and
the illumination of the light is different in at least one of color and whether the light is blinking or continuously illuminated.

20. The system of claim 17, wherein the condition is selected from the group consisting of temperature, status of a power source of the electrosurgical tool, an energy mode of the electrosurgical tool, and operational status of the electrosurgical tool.

21. The system of claim 17, wherein, with the housing removably attached to the electrosurgical tool, information received from the electrosurgical tool regarding the electrosurgical tool is configured to be stored in the memory; and
the communication mechanism is configured to communicate the information stored in the memory to the external device.

22. The system of claim 17, further comprising the electrosurgical tool.

23. The system of claim 17, wherein the electrosurgical tool includes a handpiece configured to be handheld, the controller is disposed in the handpiece, and the housing is configured to be removably attached to the handpiece of the electrosurgical tool.

24. The system of claim 17, wherein the electrosurgical tool is configured to be sterilized and reused.

25. A surgical system, comprising:
- an electrosurgical tool including handpiece configured to be handheld, and the electrosurgical tool including a controller; and
- a data module configured to be removably attached to the handpiece of the electrosurgical tool, the data module including a light and a memory;
- wherein, with the data module removably attached to the handpiece of the electrosurgical tool:
  - the controller of the electrosurgical tool is configured to control illumination of the light to indicate a condition of the electrosurgical tool, and
  - the data module is configured to receive information from the electrosurgical tool regarding the electrosurgical tool and to store the received information in the memory.

26. The system of claim 25, wherein the data module also includes a communication mechanism configured to communicate data stored in the memory to an external device.

27. The system of claim 25, wherein the data module is configured to be mechanically attached to the handpiece of the electrosurgical tool such that the data module is also communicatively coupled to the controller of the electrosurgical tool; and
- the controller is disposed in the handpiece of the electrosurgical tool.

28. The system of claim 25, wherein the electrosurgical tool is one of an orthopedic impactor, a surgical drill, and a surgical reciprocating saw.

* * * * *